United States Patent [19]
Mixson

[11] Patent Number: 6,080,728
[45] Date of Patent: Jun. 27, 2000

[54] CARRIER: DNA COMPLEXES CONTAINING DNA ENCODING ANTI-ANGIOGENIC PEPTIDES AND THEIR USE IN GENE THERAPY

[76] Inventor: A. James Mixson, 1 Baderwood Ct., Rockville, Md. 20855

[21] Appl. No.: 08/985,526

[22] Filed: Dec. 5, 1997

Related U.S. Application Data

[63] Continuation-in-part of application No. 08/680,845, Jul. 16, 1996, Pat. No. 5,815,216.

[30] Foreign Application Priority Data

Jul. 16, 1997 [EP] European Pat. Off. .............. 97112154

[51] Int. Cl.[7] ...................................................... A61K 48/00
[52] U.S. Cl. .............................................. 514/44; 424/450
[58] Field of Search ................................. 514/44; 424/450

[56] References Cited

U.S. PATENT DOCUMENTS

| | | | |
|---|---|---|---|
| 5,631,237 | 5/1997 | Dzau et al. ................................. | 514/44 |
| 5,770,581 | 6/1998 | Weichselbaum et al. ................ | 514/44 |
| 5,792,845 | 8/1998 | O'Reilly et al. ......................... | 536/23.1 |
| 5,814,618 | 9/1998 | Bujard et al. ............................. | 514/44 |
| 5,851,999 | 12/1998 | Ullrich et al. ............................ | 514/44 |

FOREIGN PATENT DOCUMENTS

| | | |
|---|---|---|
| 0443404A1 | 8/1991 | European Pat. Off. . |
| WO 92/02240 | 2/1992 | WIPO . |
| 93/16718 | 9/1993 | WIPO . |
| WO 93/16716 | 9/1993 | WIPO . |
| WO 95/29242 | 11/1995 | WIPO . |
| WO 95/30330 | 11/1995 | WIPO . |
| WO 95/31559 | 11/1995 | WIPO . |
| WO 96/21416 | 7/1996 | WIPO . |

OTHER PUBLICATIONS

TE Maione et al (1991) Cancer Research 51: 2077–2083.
N Sakamoto et al (1991) Cancer Research 51: 903–906.
MS Sheikh et al (1995) Oncogene 11: 1899–1905.
TPD Fan et al (1995) Trends Pharmaceutical Sciences 16:57–66.
I Saiki et al (1990) Japanese J Cancer Research 81:668–675.
C Clapp et al (1993) Endocrinology 133: 1292–1299.
MJ Hawkins (1995) Current Opinion in Oncology 7:90–93.
Human Gene Therapy, 6:395–405 (Apr. 1995), "Systemic Gene Therapy with p53 Reduces Growth & Metastases of a Malignant Human Breast Cancer in Nude Mice" Leslie A. Lesoon–Wood et al.
Human gene Therapy 8:177–185 (Jan. 20, 1997), "Parenteral gene Therapy with p53 Inhibits Human Breast Tumors In Vivo Through a Bystander Mechanism Without Evidence of Toxicity", M. Xu et al.
Molecular Genetics & Metabolisms 63–103–109 (1998), "Gene Therapy with P53 and a Fragment of Thrombospondin I Inhibits Human Breast Cancer in Vivo", M. Xu et al.
Molecular genetics & Metabolism 64,000–000 (1998), "In Vivo Gene Therapy with a Cationic Polymer Markedly Enhances the Antitumor Activity of Antiangiogenic Genes" M. Xu et al.
Lesoon–Wood et a., Human Gene Therapy, 6:395–405 (Apr. 1995), pp. 395–405.
Weinstat–Saslow et al., Cancer Research 54:6504–6511 (1994).
Dameron et al., Science. vol. 265;1582 (1994).
O'Reilly et al., Cell, vol. 79:315, (1994).
Millauer et al., Nature, vol. 367:576, (1994).
Pasquallni et al., Nature, vol. 380:364, (1996).
Tanaka et al., Nature Medicine, vol. 3:437 (1997).
"Vectors for Gene Therapy", Chapter 12, John Wiley and Sons (1997).
O'Reilly et al., Cell, 88:277, (1997).
Calos, TIG, vol. 12:463, (1996).
Tolsma et al., The Journal of Cell Biology, vol. 122, Jul. 1993, pp. 497–510.
Goldman et al., Nature Biotechnology, 15:462, (1997).
Boussif et al., Proc. Natl. Acad. Sci., vol. 92: 7297, (1995).
Cheng, Human Gene Therapy, 7:275, (1996).
Pasqulini et al., Nature Biotechnology, 15:542, (1997).
Park et al., Proc. Am. Ass. Canc. Res., 38, No. 2291, (Mar. 1997).

*Primary Examiner*—Bruce R. Campbell
*Attorney, Agent, or Firm*—Connolly Bove Lodge & Hutz LLP

[57] ABSTRACT

Carrier complexes comprising DNA encoding an anti-angiogenic gene or peptide and optionally a further DNA encoding a tumor suppressor protein are described. When administered to a subject bearing a tumor, the complexes can inhibit growth of the tumor.

17 Claims, 2 Drawing Sheets

Intratumoral Injections of Liposome:DNA Complexes

*, Angio vs. BAP, p<0.05

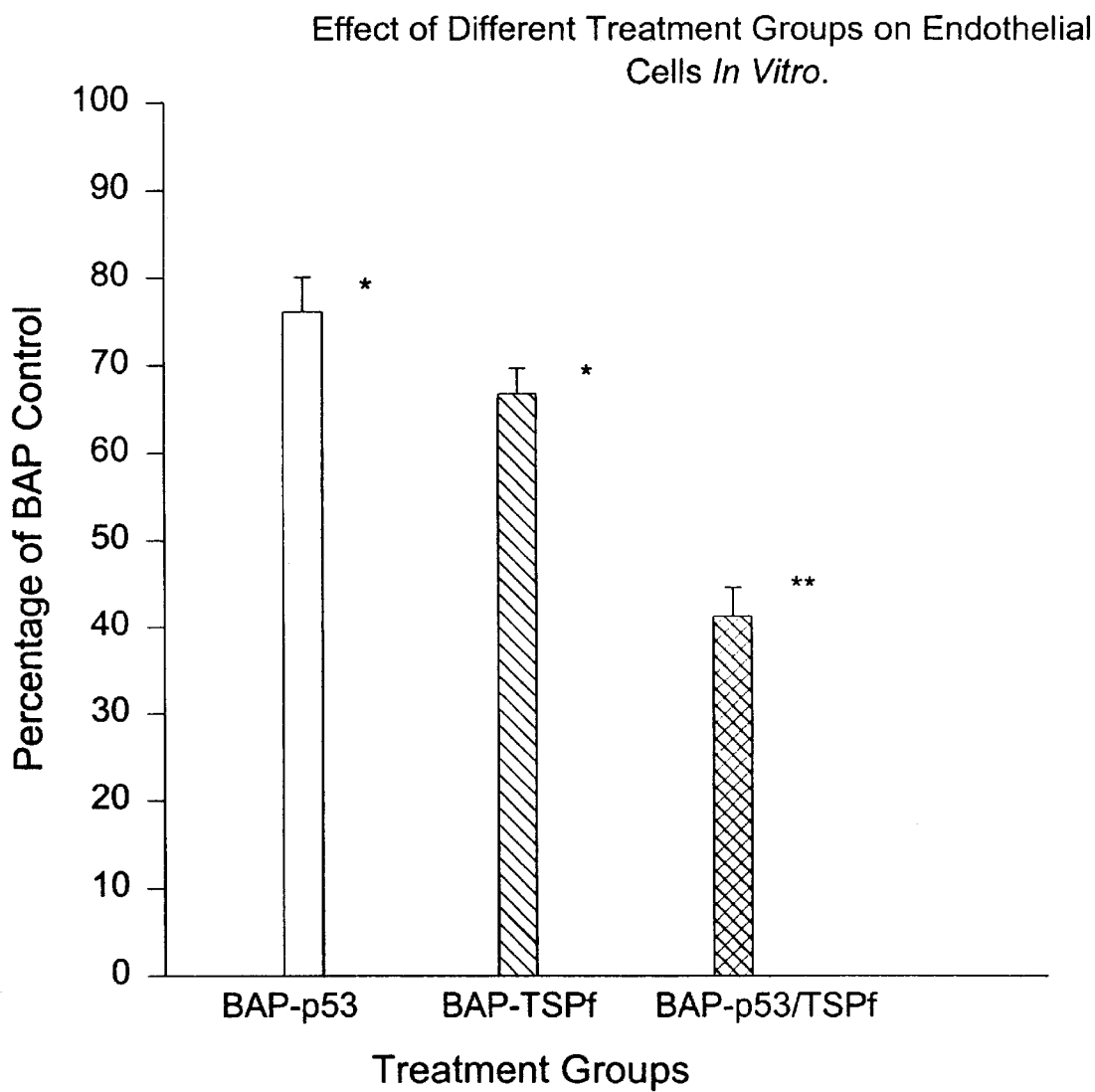

CARRIER: DNA COMPLEXES CONTAINING DNA ENCODING ANTI-ANGIOGENIC PEPTIDES AND THEIR USE IN GENE THERAPY

This application is a continuation in part of application Ser. No. 08/680,845, filed Jul. 16, 1996 now U.S. Pat. No. 5,815,216.

FIELD OF THE INVENTION

The present invention relates to delivery of antiangiogenic genes or DNA encoding anti-angiogenic peptides to a tumor in vivo, and expression of the DNA to inhibit tumoral growth. Carrier:DNA complexes are provided comprising DNA encoding at least one anti-angiogenic protein or peptide, optionally together with further DNA encoding a tumor suppressor protein. These complexes are useful in gene therapy for inhibition of tumor growth.

BACKGROUND OF THE INVENTION

I. Gene Therapy

Development of gene therapy techniques is approaching clinical realization for the treatment of neoplastic and metabolic diseases. There remains substantial need for improvement both in the vector delivery systems for delivery of the transgene to target tissues, and the identification of genes most effective for anti-tumor therapy.

Vectors for carrying genes may be viral or non-viral. For example, replication-deficient retroviral vectors can efficiently transfect dividing cells. Local intratumoral injection of retroviruses that contain a thymidine kinase transgene has been used successfully to affect regression of gliomas (Culver et al, *Science*, 2:1550–1552 (1992)). Unlike retroviral vectors, adenoviral vectors can also transfect non-dividing cells, and their ability to cause insertional mutagenesis is greatly reduced. However, they can have the undesirable potential to activate the immune system in humans (Crystal, *Science*, 270:404–410, (1995). Attempts are underway to minimize the immunogenicity of the adenoviral vectors.

Non-viral vectors of DNA include primarily liposomes, peptides, proteins and polymers (Ledley, *Current Opinion in Biotechnology*, 5:626–636 (1994)). Of these, liposomes are currently the most common non-viral vectors of DNA. The major advantage of liposomes over retroviruses is that DNA is not incorporated into the genome, and unlike adenoviral vectors, they are not immunogenic. However, the major limitation of liposomes is that they are not as efficient as viral vectors in transfecting many cell types. Until recently, their medical utility was limited by their rapid uptake by phagocytic cells. Interest in liposomes as a vector has been increased by two technological advances. First, stearically stabilized (Stealth) liposomes have been developed which are more non-reactive and are not readily taken up by the reticuloendothelial system (RES). Stealth liposomes are composed of lipids rich in oxygen in their head group (ethylene glycol or glycolipids) which provide a stearic barrier outside of the membrane. As a result, Stealth liposomes remain in the blood for up to 100 times longer than conventional liposomes, and can thus increase pharmacological efficacy (Papahajopoulos, In: Stealth Liposomes, Ed., Lasic et al, CRC Press (1995); and Lasic et al, *Science*, 267:1275–76 (1995)). However, stealth liposomes are still not particularly efficient in transfection of cells or as vectors for DNA.

The second significant advance in liposome technology has been the use of cationic liposomes complexed to negatively-charged DNA. Cationic liposomes can condense DNA, and increase transfection yields several orders of magnitude. In the cationic liposome:DNA complex, the nucleic acids or oligonucleotides are not encapsulated, but are simply complexed with small unilamellar vesicles by electrostatic interactions. The exact nature of the cationic liposome:DNA complex is not fully known, but intricate topological rearrangements of the cationic liposome:DNA complex may occur, including DNA condensation, liposome aggregation, and fusion. This supramolecular complex can be added to cells in vitro, injected parenterally, or aerosolized for pulmonary applications (Lasic et al, *Science*, 267:1275–1276 (1995)). Further, the intravenous injection into mice of high concentrations of the CAT gene (100 $\mu$g or greater) complexed with cationic liposomes has been found to result in 40% transfection efficiency of well vascularized tissues, such as the spleen (Zhu et al, *Science*, 261:209–211 (1993)). Notwithstanding these advances, a major challenge of gene therapy remains the systemic delivery of transgenes to the tumor or peritumoral area that will effectively decrease the size of primary tumors and their metastases. Unlike the spleen and bone marrow, which are highly vascular and have a high capacity to filter macromolecules from the blood stream, most organs and tumors do not have this capacity, and the transfection efficiency of these tissues with liposomes is low (Marshall, *Science*, 269:1051–1055 (1995)). In addition, another limitation of cationic liposome:DNA complexes is that their ½ life in the blood stream is normally less than one hour (Allen et al, In: *Liposome Technology*-Vol. III, Ed., Gregoriadis G et al, CRC Press (1993); Li and Huang, J. of Liposome Research, 6:589 (1996). Sufficient transfection of the target cell by vectors carrying therapeutic genes has thus far been the rate-limiting step in gene therapy.

II. Tumor Suppressor Genes

Tumor suppressor genes are well-known in the art, and include the p53 gene (Baker et al, *Science*, 249:912–915 (1990)), the p21 gene (El-Deiry et al, *Cell*, 75:817–825 (1993); and Harper et al, *Cell*, 75:805–816 (1993)), and the rb gene (Bookstein et al, *Science*, 247:712–715 (1990)).

Mutations in the tumor suppressor gene p53 are known to occur in over 50% of human tumors, including metastatic breast cancer. Various groups have found that reintroduction of the wild-type P53 by mediated transfer of a single copy of the p53 transgene into a variety of tumor cells, including breast cancer cells, results in a decrease in growth rate and/or attenuated tumor development once those transfected cells were implanted into nude mice (Wang et al, *Oncogene*, 8:279–288 (1993); Baker et al, *Science*, 249:912–915 (1990)); Bookstein et al, *Science*, 247:712–715 (1990); Cheng et al, *Cancer Res.*, 52:222–226 (1992); Isaacs et al, *Cancer Res.*, 51:4716–4720 (1991); Diller et al, *Mol. Cell. Biol.*, 10:5772–5781 (1990); Chen et al, *Oncogene*, 6:1799–1805 (1991); and Zou et al, *Science*, 263:526–529 (1994)). In addition, intratracheal injection of a retrovirus containing the p53 transgene has been shown to significantly inhibit the growth of lung tumors (Fujiwara et al, *J. Natl. Cancer. Inst.*, 86:1458–1462 (1994)).

Systemic intravenous administration of a $\beta$-actin promoter-containing vector containing the p53 coding sequence complexed to cationic liposomes has been found to affect the tumor growth of a malignant line of breast cancer cells injected into nude mice (Lesoon-Wood et al, *Proc. Am. Ass. Cancer Res.*, 36:421 (1995); and Lesoon-Wood et al, *Human Gene Ther.*, 6:39–406 (1995)). Of the 15 tumors treated in this study, four of these tumors did not respond to treatment. Because of the unresponsiveness of these tumors, new therapies were sought in the present invention to more effectively decrease the size of these tumors.

p53 coordinates multiple responses to DNA damage. DNA damage results in an increase in the level of the p53 protein. Following DNA damage, an important function of wild-type p53 function is to control the progression of cells from G1 to S phase. Recently, several groups have found that p53 transcriptionally activates a p21 kd protein (also known as WAF1 or CIP1), an inhibitor of cyclin-dependent kinases (CDKs) (El-Deiry et al, supra; and Harper et al, supra). Inhibition of CDK activity is thought to block the release of the transcription factor E2F, and related transcription factors from the retinoblastoma protein RB, with consequent failure to activate transcription of genes required for S phase entry (Harper et al, supra; and Xiong et al, *Nature,* 366:701–704 (1993)). Evidence consistent with the model that pRb is a downstream effector of p53-induced GI arrest has recently been reported (Dulic et al, *Cell,* 76:1013–1023 (1994)). Thus, p53 regulates cell cycle through two proteins: p21 and rb.

III. Anti-Angiogenic Proteins

Proteins with anti-angiogenic activities are well-known and include: thrombospondin I (Kosfeld et al, *J. Biol. Chem.,* 267:16230–16236 (1993); Tolsma et al, *J. Cell Biol.,* 122:497–511 (1993); and Dameron et al, *Science,* 265:1582–1584 (1995)), IL-12 (Voest et al, *J. Natl. Cancer Inst.,* 87:581–586 (1995)), protamine (Ingber et al, *Nature,* 348:555–557 (1990)), angiostatin (O'Reilly et al, *Cell,* 79:315–328 (1994)), laminin (Sakamoto et al, *Cancer Res.,* 5:903–906 (1991)), endostatin (O'Reilly et al., *Cell,* 88:277–285 (1997)), and a prolactin fragment (Clapp et al, *Endocrinol.,* 133:1292–1299 (1993)). In addition, several anti-angiogenic peptides have been isolated from these proteins (Maione et al, *Science,* 247:77–79 (1990); Woltering et al, *J. Surg. Res.,* 50:245–251 (1991); and Eijan et al, *Mol. Biother.,* 3:38–40 (1991)).

Thrombospondin I (hereinafter "TSPI") is a large trimeric glycoprotein composed of three identical 180 kd subunits (Lahav et al, *Semin. Thromb. Hemostasis,* 13:352–360 (1987)) linked by disulfide bonds (Lawer et al, *J. Cell Biol.,* 103:1635–1648 (1986); and Lahav et al, *Eur. J. Biochem.,* 145:151–156 (1984)). The majority of anti-angiogenic activity is found in the central stalk region of this protein (Tolsma et al, supra). There are at least two different structural domains within this central stalk region that inhibit neovascularization (Tolsma et al, supra).

Besides TSPI, there are six other proteins (fibronectin, laminin, platelet factor-4, angiostatin, endostatin and prolactin fragment) in which peptides have been isolated that inhibit angiogenesis. In addition, the dominant negative fragment of FlK1 and analogues of the peptide somatostatin are known to inhibit angiogenesis.

Fibronectin (FN) is a major surface component of many normal cells, as well as a potent cell spreading factor. During transformation, the loss of cellular FN has been observed. Furthermore, the addition of fibronectin to transformed cells restores the normal phenotype. It has been found that either heparin-binding or cell-adhesion fragments from FN can inhibit experimental metastasis, suggesting that cell surface proteolyglycans are important in mediating the adhesion of metastatic tumor cells (McCarthy et al, *J. Natl. Cancer Inst.,* 80:108–116 (1988)). It has also been found that FN and one of its peptides inhibits in vivo angiogenesis (Eijan et al, *Mol. Biother.,* 3:38–40 (1991)).

Laminin is a major component of the basement membrane, and is known to have several biologically active sites that bind to endothelial and tumor cells. Laminin is a cruciform molecule that is composed of three chains, an A Chain and two B chains. Several sites in laminin have been identified as cell binding domains. These sites promote cellular activities in vitro, such as cell spreading, migration, and cell differentiation. Two peptides from two sites of the laminin B1 chain are known to inhibit angiogenesis (Grant et al, *Path. Res. Pract.,* 190:854–863 (1994)).

Platelet factor-4 (PF4) is a platelet α-granule protein originally characterized by its high affinity for heparin. The protein is released from platelets during aggregation as a high molecular weight complex of a tetramer of the PF4 polypeptide and chondroitin sulfate, which dissociates at high ionic strength. PF4 has several biological properties including immunosuppression, chemotactic activity for neutrophils and monocytes as well as for fibroblasts, inhibition of bone resorption, and inhibition of angiogenesis. The angiostatic properties of human PF4 are associated with the carboxyl-terminal, heparin binding region of the molecule. A 12 amino acid synthetic peptide derived therefrom has been discovered to have marked angiostatic affects (Maione et al, *Science,* 247:77–79 (1990)).

Endostatin is a 20 kDa protein fragment of collagen XVIII. It has recently been found to be a potent inhibitor of tumor angiogenesis and tumor growth (O'Reilly et al., *Cell,* 88, 277–285, 1997).

Although somatostatin is not a protein, it is a naturally-occurring cyclic 14 amino acid peptide whose most-recognized function is the inhibition of growth hormone (GH) secretion. Somatostatin is widely distributed in the brain, in which it fulfills a neuromodulatory role, and in several organs of the gastrointestinal tract, where it can act as a paracrine factor or as a true circulating factor. The role played by the neuropeptide somatostatin, also known as somatotropin release inhibitory factor (SRIF), in human cancer is not well understood. Recent investigations involving somatostatin receptors in normal and neoplastic human tissues suggest that the action is complex, and involves both direct and indirect mechanisms. One of the anti-tumor mechanisms of these synthetic somatostatin analogues may be an anti-angiogenic effect (Woltering et al, *J. Surg. Res.,* 50:245–50 (1990)). In a recent study, the ability of native somatostatin and nine somatostatin analogues to inhibit angiogenesis were evaluated. The most potent somatostatin analogue was found to be approximately twice as potent as the naturally-occurring somatostatin (Barrie et al, *J. Surg. Res.,* 55:446–50 (1993)).

Angiostatin is a 38 kDa polypeptide fragment of plasminogen. Whereas plasminogen has no fibrinogenic activity, angiostatin has marked angiogenic activity (O'Rielly MS, et al *Cell,* 79:315–28 (1994)). Angiostatin was isolated when it was observed that the primary tumor suppressed metastases. That is, when the primary tumor was removed, the metastases grew. Administration of angiostatin blocks neovascularization and growth of metastases.

The Flk1 receptor is a receptor for vascular endothelial growth factor (VEGF). FlK-1 is exclusively expressed on the surface of the endothelial cells. Once VEGF binds to the receptor, the Flk-1 receptor then homodimerizes to stimulate the endothelial cell to divide. If a mutant receptor of Flk-1 is transfected into the endothelial cells, the mutant receptor dimerizes with the wild-type Flk-1 receptor. In this endothelial transfected with the mutant Flk-1 receptor, VEGF is unable to stimulate the endothelial cells to divide. Co-administration of a retrovirus carrying the Flk-1 cDNA (Millauer B. et a., Nature, 367, 1994) inhibits tumor growth. This emphasizes that the receptor plays a critical role in the angiogenesis of solid tumors.

Finally, a 16 kd fragment of prolactin has been found to be antiangiogenic. Similar to plasminogen, prolactin is not anti-angiogenic but the prolactin fragment is a potent in vivo and in vitro inhibitor of angiogenesis (Clapp C. et al. *Endocrinology.* 133:1292–1299 (1993).

Despite the evidence that anti-angiogenic peptides can be useful anti-tumor agents, and interest in targeting genes toward the vasculature, there have been no published reports on effective in vivo gene therapy regimens utilizing anti-angiogenic DNA sequences.

The only transfected antiangiogenic gene that has been shown to inhibit tumor growth is full length thrombospondin I. In that study (Weinstat-Saslow et al, *Cancer Research* 54, 6504–6511, (1994)) tumor cells that expressed 15-fold higher levels of the thrombospondin I in vitro than baseline cells were implanted into mice. This transfected full length thrombospondin I was secreted from the tumor cells, and effectively reduced the tumor by 60%. Thus, this study determined that transfection of 100% of the tumor cells with a highly expressed and secreted antiangiogenic gene was able to reduce tumor size.

SUMMARY OF THE INVENTION

An object of the invention is to deliver anti-angiogenic genes and/or DNA encoding anti-angiogenic peptides to a tumor site in vivo, preferably by injection, whereby the DNA is expressed at the site of the tumor to inhibit tumoral growth.

A further object of the present invention is to provide carrier complexes containing DNA encoding anti-angiogenic peptides. The carrier may be specifically targeted to the tumor and/or to the tumor vasculature. The complexes are useful for providing anti-angiogenic gene therapy and inhibiting tumor growth in a subject.

A further object of the present invention is to provide carrier complexes containing DNA encoding an anti-angiogenic gene or peptide, or DNA encoding more than one anti-angiogenic gene or peptide, and additionally DNA encoding a tumor suppressor gene.

In currently preferred embodiments, the carrier material comprises complexes of cationic polymer or cationic liposomes and DNA encoding one or more antiangiogenic peptides, optionally with DNA encoding a tumor suppressor gene.

The complexes are administered in a tumor-inhibiting effective amount to a patient, preferably by injection of the complexes.

DESCRIPTION OF THE DRAWINGS

FIG. 2 is a graph showing the results of in vitro transfection experiments into endothelial cells using cationic polymer carrier complexed with DNA encoding anti-angiogenic peptides, as described in Example 10.

DETAILED DESCRIPTION OF THE INVENTION

Figure 1:
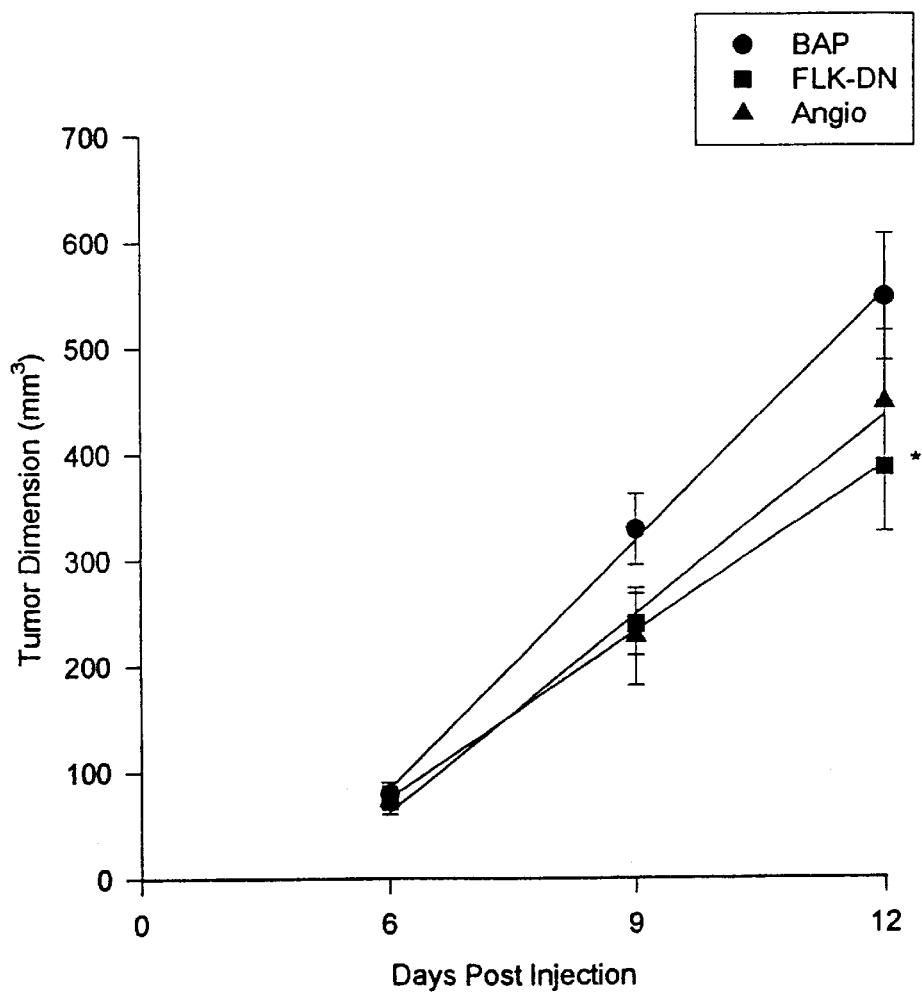
FIG. 1 is a graph depicting the results of the experiment described in Example 8, infra, wherein complexes containing DNA encoding anti-angiogenic peptides were administered intratumorally.

In one embodiment, the above-described objects of the present invention have been met by a carrier:DNA complex comprising DNA encoding at least one anti-angiogenic gene or peptide and optionally additional DNA encoding a tumor suppressor protein. The DNA may encode a full-length anti-angiogenic protein, or may encode a peptide having antiangiogenic activity, or a combination of DNAs.

Preferred carrier vehicles are liposomes, polymers, viruses (retroviruses and adenoviruses, for example), viral shells, micelles, microspheres and the like. See, e.g. Nabel, E., Vectors for Gene Therapy, in Current Protocols in Human Genetics on CD-ROM, John Wiley and Sons (1997) The carrier used in the invention is selected such that it can deliver the DNA in vivo to a tumor and/or the peritumoral area, including tumor vasculature, in a manner such that the DNA can be expressed.

Liposome carriers are known in the art. Reference is made to, for example, Liposome Technololy, 2d Edition, CRC Press: Boca Raton (1983); and Stealth Liposomes, Lasic and Martin, Eds., CRC Press: Boca Raton (1995). Examples of cationic lipids include 1,2-dioleolyl-sn-glycero-3-ethylphosphocholine (Avanti, Birmingham, Ala.), 1,2-dimyristoyl-sn-glycero-3-ethylphosphocholine (Avanti, Birmingham, Ala.), and (2,3-diol-eyloxy)propyl-N,N,N-trimethylammonium chloride (DOTMA) (Syntex Corp., Palo Alto, Calif.).

The cationic lipids may be used in a mixture with dioleoylphosphatidylethanolamine (DOPE) (Avanti, Bimingham, Ala.). In the cationic liposome embodiment, the amount of cationic lipid present in the mixture is generally in the range of from 100 to 40 mol %, preferably about 50 mol %. The amount of DOPE present in the mixture is generally in the range of from 0 to 60 mol %, preferably about 50 mol %.

The liposomes may contain lipid derivatives of polyethylene glycol (PEG), referred to herein as "pegylated lipids". Components useful in creating pegylated lipids include, for example, 1,2-diacyl-sn-glycero-3-phosphoethanolamine-N-[poly(ethylene glycol) 2000]. If pegylated lipid components are present, they are generally included in amounts of 0 to 10 mol %, preferably 1 to 5 mol %.

Cationic liposomes are prepared in a manner similar to other liposomes, for example, the cationic lipids with/or without DOPE are dissolved in a solvent, e.g., chloroform. The lipids are then dried in a round bottom flask overnight on a rotary evaporator. The resulting lipids are then hydrated with sterile water over a 1 hr period to form large multilamellar vesicle liposomes. To decrease the size of the liposomes, one may sonicate or pass the liposomes back and forth through a polycarbonate membrane. The DNA is then added to a solution containing the liposomes after their formation.

Cationic polymer carriers useful in the context of this invention include polyethyleneimime (available from Avanti Lipids), polylysine (available from Sigma), polyhistidine (Sigma), and Superfect (available from Qiagen). Use of cationic polymer carriers for gene delivery in vitro and in vivo has been described in the literature, for example, by Goldman et al., Nature BioTechnology, 15:462 (1997).

Stealth liposomes concentrate in solid tumors possibly due to their "leaky" vessels. Although stealth liposomes' uptake into cells is decreased due to the pegylation of their surface, this decrease is more than offset by their prolonged half-life in the circulation. Thus, pegylated liposomes are good carriers of DNA. Micelles are closely related to liposomes except they lack a bipolar membrane. They are made up of polar lipids, some of which can be the same cationic lipids utilized in liposomes. Similar to liposomes, micelles are known to transfect cells with plasmid DNA (Zhang YP. Et al., Pharmaceutical Res. 14:190–6, 1997; Labat-Moleur F. et al., Gene Therapy 3:1010–7, 1996).

As known in the art, there are potential problems with the intravenous injection of viral vectors. However, viruses can deliver transgenes by regional intra-arterial and/or intratumoral injections. Construction of viral vector carrying transgenes has been extensively described and they have been used successfully in gene therapy. (Nable, E. In "Current Protocols in Human Genetics on CD-ROM", John Wiley & Sons, Inc. 1997).

Delivery of the complexes to a target in vivo can be enhanced by including a ligand in the complex having affinity for a specific cellular marker. Ligands include antibodies, cell surface markers, viral peptides, and the like, which act to home the complexes to tumor vasculature or endothelial cells associated with tumor vasculature, or to tumor cells themselves, if a secreted form of the antiangiogenic DNA is delivered. An antibody ligand may be an antibody or antibody fragment specific towards a tumor marker such as Her2, CEA, ferritin receptor, or a marker associated with tumor vasculature (integrins, tissue factor, or β-fibronectin isoform). Antibodies or other ligands may be coupled to carriers such as liposomes and viruses, as is known in the art. See, e.g., Neri et al., Nature BioTechnology, 15:1271 (1997); Kirpotin, D. et al., Biochemistry 36:66 (1997) Cheng, Human Gene Therapy, 7:275 (1996); Pasqualini et al., Nature Biotechnology, 15:542 (1997); and Park et al., Proc. Am. Ass. Canc. Res. 38:342 (1997); Mori and Haung supra; and Nabel, supra. Alternatively, psuedotyping of a retrovirus may be used to target a virus towards a particular cell. Marin et al., Mol. Med. Today, 3:396 (1997).

In a further embodiment, the complexes further include a tumor suppressor gene. Examples of such tumor suppressor genes include the p53 gene, the p21 gene (El-Deiry et al, supra; and Harper, supra), and the rb gene (Bookstein et al, supra). The p53 gene is the currently preferred tumor suppressor gene.

The particular anti-angiogenic protein or peptide encoded by the anti-angiogenic DNA is not critical to the present invention. Examples of suitable peptides include:

(i) a fragment of thrombospondin I (TSPf) having the amino acid sequence shown in SEQUENCE ID NO: 1. This fragment is encoded by the DNA sequence (nucleotides 1013–1650 of the TSPI gene) shown in SEQUENCE ID NO: 2.

ii) a concatamer of TSPf having the amino acid sequence of SEQUENCE ID NO: 3, which is encoded by the DNA sequence shown in SEQUENCE ID NO: 4.

iii) laminin peptide having the amino acid sequence shown in SEQUENCE ID NO. 5, which is encoded by the DNA sequence shown in SEQUENCE ID NO. 6.

iv) a concatamer of the laminin sequence having the amino acid sequence shown in SEQUENCE ID NO: 7, which is encoded by the DNA sequence shown in SEQUENCE ID NO: 8.

v) a peptide from platelet factor-4 having the amino acid sequence shown in SEQUENCE ID NO: 9, which is encoded by the DNA sequence shown in SEQUENCE ID NO: 10.

vi) a concatamer of the platelet factor-4 peptide having the amino acid sequence shown in SEQUENCE ID NO: 11, which is encoded by the DNA sequence shown in SEQUENCE ID NO: 12.

vii) a somatostatin inhibitor peptide having the amino acid sequence shown in SEQUENCE ID NO: 13, which is encoded by the DNA sequence shown in SEQUENCE ID NO: 14.

viii) a concatamer of somatostatin inhibitor having the amino acid sequence shown in SEQUENCE ID NO: 15, which is encoded by the DNA sequence shown in SEQUENCE ID NO: 16.

ix) fibronectin inhibitor peptide having the amino acid sequence shown in SEQUENCE ID NO: 17, which is encoded by the DNA sequence shown in SEQUENCE ID NO: 18.

x) a concatamer of fibronectin inhibitor peptide having the amino acid sequence shown in SEQUENCE ID NO: 19, which is encoded by the DNA sequence shown in SEQUENCE ID NO. 20.

xi) angiostatin peptide having the amino acid sequence shown in SEQUENCE ID NO: 21, which is encoded by the DNA sequence shown in SEQUENCE ID NO: 22.

xii) a concatamer of angiostatin peptide having the amino acid sequence shown in SEQUENCE ID NO: 23, which is encoded by the DNA sequence shown in SEQUENCE ID NO: 24.

xiii) prolactin peptide having the amino acid sequence shown in SEQUENCE ID NO: 25, which is encoded by the DNA sequence shown in SEQUENCE ID NO: 26.

xiv) a concatamer of prolactin peptide having the amino acid sequence shown in SEQUENCE ID NO. 27, which is encoded by the DNA sequence shown in SEQUENCE ID NO: 28.

xv) a peptide of Flk-1-DN having the sequence shown in SEQUENCE ID NO: 34, which is encoded by the DNA shown in SEQUENCE ID NO. 35.

xvi) a peptide of endostatin having the sequence shown in SEQUENCE ID NO: 36, which is encoded by the DNA shown in SEQUENCE ID NO: 37.

The above sequences are exemplary and not limiting on the scope of the invention. Certain domains of these fragments are known to have antiangiogenic activity, as reported in the literature. As will be apparent, some of these sequences are concatameric. Use of concatamers can increase the anti-angiogenic dosage level without changing the amount of vector necessary for delivery. The concatamers can extend up to approximately 4400 bases in length (the coding region of a large protein), and the number of concatamers possible will depend on the number of bases of a single anti-angiogenic peptide-encoding unit. As seen in the above examples, the concatamer repeats can be separated by intervening sequences.

For fibronectin, the range of concatamers would be about 2 to about 66. Although the maximum number of anti-angiogenic units for the TSPf is about 6, one can increase this concatameric number by deleting sequence less material to anti-angiogenic effects, such as the sequence shown in SEQUENCE ID NO: 29, where the corresponding amino acid sequence is shown in SEQUENCE NO: 30. In a similar manner, the concatameric number of the platelet factor-4 peptide, somatostatin inhibitor, angiostatin, and prolactin can be modified and increased.

Since more than one anti-angiogenic pathway exists, concatamers consisting of two or more types of inhibitor could be more effective than homogenous concatamers. For example, heterogeneous concatamers of TSPI and the fibronectin inhibitors can be inserted into the same vector. An example of such a heterogenous concatamer encoding DNA is shown in SEQUENCE ID NO: 31. In such heterogenous concatamers, the peptide-encoding repeats of each sequence may be linked in blocks and/or randomly.

The heterogeneous concatamers need not be limited to only anti-angiogenic peptides. For example, the protein angiostatin or the large polypeptide fragment of prolactin can be modified with genes encoding anti-angiogenic peptides. Again, the concatameric number will vary depending on the number of nucleotide bases of the unit angiogenic inhibitor. In a concatamer of large and small anti-angiogenic inhibitors, the ratio of large to small inhibitors is 0.1 to 0.9, preferably 1:1.

A translational start signal Met is included in the peptides as well as a transcriptional stop codon (TAA).

The SalI sites present in the above-sequences are a useful cloning tool for insertion of the DNA into a vector, for example BAP vector, which is known to be useful for expressing proteins efficiently in vivo from the β-actin promoter (Ray et al, *Genes Dev.*, 5:2265–2273 (1991)). Other restriction sites can be incorporated into the DNA for cloning into other vectors, as those in the art will readily appreciate.

Other useful vectors for containing the DNA sequences include plasmids with a simian viral promoter, e.g., pZeoSV (Invitrogen); the CMV promoter, e.g., pcDNA3, pRc/CMV or pcDNA1 (Invitrogen); or the phosphoglycerate kinase (PGK) promoter (Abud et al., Developmental Genetics, 19:51 (1996). Plasmids with a CMV promoter may contain an intron 5' of the multiple cloning site (Zhu et al, supra). Plasmids containing the BGH terminator instead of the viral SV40 polyA terminator, e.g., pcDNA3, pRc/CMV, pRc/RSV (Norman et al, IBC's 5th Annual Meeting (1995); and Invitrogen vectors), can also be employed in the present invention so as to increase the expression of the tumor suppressor gene and the anti-angiogenic peptide(s) in targeted cells.

Expression of the DNA encoding the tumor suppressor protein and the DNA encoding the anti-angiogenic peptide can be achieved using a variety of promoters. For example, the promoter can be a generalized promoter, such as the β-actin promoter, a simian viral promoter, or the CMV promoter, or a tissue specific promoter, such as the α-fetal protein promoter which is specific for liver (Kaneko et al, *Cancer Res.*, 55:5283–5287 (1995), the tyrosinase promoter which is specific for melanoma cells (Hughes et al, *Cancer Res.*, 55:3339–3345 (1995); or the enolase promoter which is specific for neurons (Andersen et al, *Cell. Molec. Neurobiol.*, 13:503–515 (1993)).

The plasmid vector may contain multiple promotors to enhance expression efficiency. Moreover, a plasmid vector may include IRES sequence (internal ribosome entry site) between different DNA coding sequences, allowing for the translation of more than one peptide from the same transcript. Coding sequences can be associated with secretory sequences in the vector to enhance expression levels. In a further embodiment of the invention, the vector may comprise an extrachromosomal replicating vector. See, e.g. Calos, TIG 12:463 (1996). These and other techniques to optimize expression are known to those in the art.

The particular amount of DNA included in the complexes of the present invention is not critical, the amount of total DNA administered in the complexes generally being in the range of about 0.005 to 0.32 μg/pM of carrier, preferably 0.045 to 0.08 μg/pM of carrier.

The DNA encoding a tumor suppressor gene is generally present in an amount of from 0.0025 to 0.16 μg/pM of carrier, preferably 0.028 to 0.04 μg/pM of carrier. The DNA encoding an anti-angiogenic peptide is generally present in an amount from 0.0025 to 0.16 μg/pM of carrier, preferably 0.028 to 0.04 μg/pM of carrier.

The mole ratio of the DNA encoding the tumor suppressor gene to the DNA encoding the anti-angiogenic peptide is also variable. Generally, the mole ratio is between 1:5 to 5:1, preferably about 1 to 1.

The DNA encoding the tumor suppressor gene and the anti-angiogenic peptide may be contained on the same vector or on separate vectors. Different DNAs encoding anti-angiogenic peptides may be provided on the same or different vectors within the complexes.

In another embodiment, the above-described objects of the present invention have been met by a method for inhibiting tumor growth in a subject comprising administering to a tumor-bearing subject a carrier:DNA complex comprising DNA encoding an anti-angiogenic protein or peptide(s) with or without additional DNA encoding a tumor suppressor gene.

It is possible to treat different types of tumors. Examples of tumors which can be treated in accordance with the present invention include solid tumors, e.g., lung, colon, brain, breast and melanoma tumors. All of these tumors are very dependent on blood supply to sustain their growth.

The particular mode of administering the carrier:DNA complex of the present invention depends on various factors, but preferred modes include intravenous, subcutaneous or intratumoral injection. Intravenous injection is the preferred administration mode for distribution of the complex to the developing blood vessels of the tumor.

The amount of the carrier:DNA to be administered will vary depending upon the age, weight, sex of the subject, as well as the tumor volume and rate of tumor growth in the subject. Generally, the amount of DNA to be administered will be about 1 to 60 μg, preferably about 5 to 16 μg.

The following examples are provided for illustrative purposes and should not be construed as limiting the scope of the invention.

Materials

Production of DNA Vectors

A. TSPI Vector

The coding region of the TSPI gene is known (GB Accession code-X14787). The TSPI gene was inserted into the XbaI site of BAP vector (Ray et al, supra), producing TSPI vector, in which expression of the TSPI gene is controlled by the β-actin promoter.

More specifically, TSPI cDNA and Bluescript plasmid (Promega) were digested with HindI and XbaI, and then the TSPI cDNA was ligated into Bluescript. Next, Bluescript containing the TSP cDNA and BAP vector were digested with SalI and BamHI, and TSPI cDNA inserted in the XbaI site of BAP vector. The correct orientation of the TSPI gene in BAP vector was confirmed by DNA sequencing.

B. TSPf Vector

TSPf vector is a vector containing a DNA fragment of the TSPI gene which has the two anti-angiogenic domains (nucleotides 992–1650) (Tolsma et al, supra), and a start codon and a stop codon.

The DNA fragment was prepared by PCR using thrombospondin I cDNA as template, and 100 pmoles of each of the following primers 5'-TAGG TCTAGAATGACTGAAGAGAACAAAGAG-3' (SEQUENCE ID NO: 32) and 5'-ATGG TCTAGATTAGAGACGACTACGTTTCTG-3' (SEQUENCE ID NO: 33) to amplify nucleotides 1013 to 1650 of the TSPI gene. Both primers contain XbaI sites (underlined), the first primer contains an ATG start codon (in bold), and the second primer contains a TTA stop codon (reverse orientation in bold).

The resulting 638 base pair fragment of the TSPI gene (hereinafter "TSPf") encodes peptides that are known to be angiogenic inhibitors (Tolsma et al, supra).

After amplification, the DNA fragment was purified, digested with XbaI, and the digested fragment inserted into the XbaI site of BAP vector such that the expression of the TSPf gene was controlled by the β-actin promoter (Ray et al, supra; and Lesoon-Wood et al, Human Gene Ther., 6:395–405 (1995)). The correct orientation of the fragment in BAP vector was verified by digestion with BamHI, and confirmed by DNA sequencing.

C. p53 Vector

The coding sequence of the p53 gene was cut from plasmid p1SVhp53c62 (Zakut-Houri et al, EMBO J., 4:1251–1255 (1985)) with XbaI, and inserted into the multiple cloning sites of pGEM3Z vector (Promega, Madison, Wis.). Digestion of the resulting vector with SAlI and BamHI generated a 1900 bp fragment that was then inserted into the SalI and BamHI sites of BAP vector such that expression of the p53 gene was controlled by the β-actin promoter. The correct orientation of the p53 gene in BAP vector was confirmed by DNA sequencing.

D. Laminim peptide vector was prepared by annealing together the following two oligonucleotides:

5'-CTATCGTCGACATGTATATTGGTTCTCGTTAAG TCGACCTATC-3' (SEQUENCE ID NO: 38) and

5'-GATAGGTCGACTTAACGAGAACCAATATACAT GTCGACGATAG-3' (SEQUENCE ID NO. 39), which contain an anti-angiogenic fragment from laminin, start and stop codons, and XbaI restrictions sites. The annealed oligonucleotides were then digested with XbaI, and inserted into the XbaI site of BAP vector. The plasmid was sequenced to verify correct orientation.

E. Angiostatin vector was prepared by amplifying the angiostatin coding sequence of plasminogen cDNA using the following primers:

5'-AGTATCTAGAATGAGTGTATCTGTCACAATG-3' (SEQUENCE ID NO: 40) and

5'-GAATTCTAGATCACCTATGAGGGGTTTGCTC-3' (SEQUENCE ID NO: 41) The resulting amplified fragment, which contained a genetically engineered ATG start site and a TAA stop codon, was digested with XBAI, purified, and inserted into the XbaI site of BAP vector. The plasmid was sequenced to verify correct orientation.

F. Laminin peptide concatame Mector was prepared by initially annealing the following two oligonucleotides:
5'-CTATCGTCGACATGTATATTGGTTCTCGTAAAAGA TATATTGGTTCTCGTGGTAAAAGAGATATT GGTTCTCGTGGTAAAAGATAAGTGACCTATC-3' (SEQUENCE ID NO: 42) and 5 '-GATAGGTCGACTTAT-3' (SEQUENCE ID NO: 43). The former oligonucleotide contains an anti-angiogenic fragment from laminin repeated four times, start and stop codons, as well as XbaI restrictions sites. The annealed oligonucleotides were then extended with PFU (Stratagene), digested with SalI, and inserted into the SalI site of BAP vector. The plasmid was sequenced to verify correct orientation.

Preparation of Cationic Liposome:DNA Complexes

A DOTMA:DOPE liposome mixture is known to efficiently transfect endothelial cells in vitro (Tilkins et al, Focus, 16:117–119 (1994)). Accordingly, liposome:DNA complexes were prepared using DOTMA:DOPE, in a 1:1 ratio, essentially as described by Debs et al, J. Biol. Chem., 265:10189–10192 (1990). Similar liposomes preparations can be prepared by mixing, at a 1:1 ratio, DOPE with other cationic lipids, such as, 1,2-dioleolyl-sn-glycero-3-ethylphophocholine, and 1,2-dimyristoyl-sn-glycero-3-ethylphophocholine.

More specifically, a mixture of 400 nmoles of the DOTMA and DOPE were dried overnight on a rotary evaporator. Then, the lipids were rehydrated with 1.5 ml of water for 2 hrs. Next, the milky liposome preparation was sonicated with a bath sonicator until clear. The resulting liposome preparation was then passed through a 50 nm polycarbonate filter between 15 to 20 times with a LipsoFast-Basic extruder (Avestin, Ottawa, On).

The DNA (see following examples) was prepared with the maxi Qiagen kits (Qiagen Inc., Chatsworth, Calif.), and washed twice in 70% (v/v) ethanol. The DNA was then washed with distilled water or dialyzed against water for 24 hrs to removed any remaining salt.

About 400 pmols of the liposome preparation was gently mixed with between 10 to 35 μg of total DNA in an Eppendorf tube. This amount in each eppendorf tube was sufficient for two injections. The same amount of DNA was injected in the combination therapies as in the single treatment regimens. For example, if 16 μg of DNA in the combination therapy (8.0 μg of p53+8.0 μg of TSPf) was injected into each mouse of one group, then 16 μg of p53 was injected into each mouse of a second group.

EXAMPLE 1

The anti-angiogenic effects of carrier:DNA complexes were evaluated in mice containing MDA-MB-435 breast cancer tumors (American Type Tissue Culture, Bethesda, Md.), which are p53 deficient.

More specifically, after administering the anesthetic, Metofane, to 126 female athymic nude mice(NCI), the mice were injected with $2.0 \times 10^5$ MDA-MB-435 tumor cells into the mammary fat pad using a stepper (Tridak) and a 27.5 g needle. Two weeks later, the mice whose tumors grew were divided into various treatment regimens, 18 mice per each regimen. The treatment regimens were as follows: (1) untreated; (2) empty BAP vector; (3) TSPI vector alone; (4) TSPf vector alone; (5) p53 vector alone; (6) p53 vector+TSPI vector; and (7) p53 vector+TSPf vector. The mice received two intravenous injections, the first injection 14 days after the malignant cells had been implanted into the mice, and the second injection 24 days after the malignant cells had been implanted into the mice. The first injection consisted of 200 pmoles of the liposomes complexed with 16 μg of total DNA. The second injection consisted of 200 pmols of the liposomes complexed with 12.0 μg of total DNA. The sizes of the tumors were measured 7 days after the second injection. The results are shown in Table 1 below.

TABLE 1

Anti-tumor Effects of TSPI and TSPf

| Putative Anti-tumor DNA | Tumor Size (mm³) |
| --- | --- |
| Untreated | 113.5 ± 6.41 |
| BAP | 102.9 ± 6.83 |
| TSPI | 103.2 ± 8.96 |
| TSPf | 89.4 ± 11.06 |
| p53 | 80.1 ± 12.7* |
| p53 + TSPI | 82.9 ± 6.95* |
| p53 + TSPf | 53.2 ± 8.37** |

*p53 or p53 + TSPI vs. untreated, $p < 0.05$
**p53 + TSPf vs. untreated or BAP, $p < 0.01$ As shown in Table 1 above, the p53-treated group was found to be statistically different from the untreated group (p<0.05) after 2 injections. However, the p53 treated group was not statistically different from the empty BAP vector group. This was similar to the results described by Lesoon-Wood et al, *Human Gene Ther.*, 6:395–406 (1995), in which p53 was not statistically different from the empty BAP vector group until after 5 injections.

However, p53 in combination with TSPf reduced tumors more effectively than p53 alone. After just 2 injections of this combination therapy, there was a 35% further reduction in tumor growth compared to p53 alone. The combination group was statistically different from both the untreated and the empty BAP vector groups (p<0.01). Although TSPf by itself was slightly less effective than p53, TSPf was, unexpectedly, substantially more effective than TSPI. In fact, the full length TSPI-treatment group had no more effect than either the empty vector or the untreated groups. This was unexpected for several reasons: 1) both the full length and the fragment of thrombospondin I contained the anti-angiogenic peptide, and 2) in a previous ex vivo study (Weinstat-Saslow et al, supra) full length thrombospondin I was effective in inhibiting tumor growth.

EXAMPLE 2

A second experiment was carried out to determine whether the combination therapy of p53 and TSPf was effective at lower dosages, and to confirm that the combination of p53 and TSPf reduced the tumor size significantly more than p53 alone.

More specifically, 36 mice were injected with $2.0 \times 10^5$ MDA-MB-435 tumor cells into the mammary fat pad. Two weeks later, the mice whose tumors grew were divided into various treatment regimens, 12 mice per each regimen. The treatment regimens were as follows: (1) empty BAP vector; (2) p53 vector alone, and (3) p53 vector+TSPf vector. The mice were injected intravenously with 200 pmols of the liposomes complexed with 8.0 µg of total DNA. Subsequently, the mice were treated in the same manner with 200 pmols of the liposomes completed with 12 µg of total DNA for the next 4 injections. Ten days elapsed between each injection. The sizes of the tumors were measured before each injection and 7 days after the last injection. The results are shown in Table 2 below:

TABLE 2

Anti-tumor Effects of p53 and TSPf

| Putative Anti-tumor DNA | Tumor Size (mm³) |
|---|---|
| BAP | 855 ± 345 |
| p53 | 616 ± 142 |
| p53 + TSPf | 265 ± 133* |

*p53 + TSPf vs. BAP, p < 0.02

As shown in Table 2 above, the combination therapy with p53 and TSPf was statistically different from BAP, whereas the p53 alone treatment was not. This experiment confirmed that p53 and TSPf can be more effective than p53 alone. Furthermore, a different dosage regimen, without an initial booster dose of 16 µg of DNA as used in the experiment in Table 1, accentuated the difference between the combination treatment and the p53 alone treatments.

EXAMPLE 3

The experiment of Example 2 was repeated to confirm that BAP-TSPf complexed to liposomes effectively inhibited the growth of implanted tumors. Five injections of the liposome:DNA complex was administered intravenously to three groups: 1) BAP, 2) TSPF, or 3) p53. Results are shown in Table 3.

TABLE 3

Antitumor Effects of TSPf

| Putative Anti-tumor genes | Tumor Size (mm³) |
|---|---|
| BAP | 619 ± 65 |
| TSPf | 386 ± 35* |
| P53 | 419 ± 26* |

*TSPF vs. BAP p < 0.05
p53 vs. BAP, p < 0.05

After five intravenous injections at a dose of 14.5 µg, the TSPf treatment group was statistically different form the BAP group.

EXAMPLE 4

An experiment was carried out to investigate the efficacy of complexes carrying DNA encoding anti-angiogenic peptide fragments of angiostatin and laminin.

126 mice injected with MDA-MB-435 tumor cells as described in Example 2 were treated as follows: (1) BAP vector; (2) TSPf vector alone; (3) laminin peptide vector alone; and (4) angiostatin vector alone. The mice received 4 intravenous injections, the first injection being 10 days after the malignant cells had been implanted into the mice, and the remaining injections were thereafter 10 days apart. The injections consisted of 200 pmols of the liposomes complexed with 12.5 µg of total DNA.

The results are shown in Table 4 below.

TABLE 4

| Putative anti-tumor DNA | Tumor Size (mm³) |
|---|---|
| BAP | 194.7 ± 11.9 |
| TSPf | 135.9 ± 11.9* |
| Laminin peptide | 126.4 ± 8.4 |
| Angiostatin | 95.2 ± 6.3*,** |

*TSP., Laminin peptide, and Angiostatin vs. BAP, p < 0.05
**Angiostatin vs. BAP, p < 0.01

As shown in Table 4 above, the cationic liposomes containing DNA encoding anti-angiogenic peptides (TSPf, laminin peptide and angiostatin) significantly inhibited tumor growth.

EXAMPLE 5

MCF7 cells (American Type Tissue Culture, Bethesda, Md.), which are a breast cancer cell line with two normal p53 alleles, were evaluated as described above except that $4.0 \times 10^6$ cells were injected into the mice and the third injection contained 12 µg of the DNA. Each injection was 10 days apart. Nine mice were injected with each of the following treatments except for regimen (1), in which 8 mice were treated: (1) untreated; (2) BAP; (3) p53; and (4) p53+TSP. The sizes of the tumors were measured 7 days after the third injection. The results are shown in Table 5 below.

TABLE 5

Effect of p53 and TSP. on MCF7s Cells

| Putative Anti-tumor Genes | Tumor Size (mm³) |
| --- | --- |
| Untreated | 124.6 ± 7.3 |
| BAP | 136 ± 16.8 |
| p53 | 83.1 ± 13.6* |
| p53 + TSPf | 69.0 ± 13** |

*p53 vs. untreated or BAP, $p < 0.05$
**p53 + TSPf vs. untreated or BAP, $p < 0.01$ As shown in Table 5 above, the most effective therapy against MCF7 was p53 and TSPI. The significance level for the p53+TSPf therapy was greater than for p53 alone when they were compared against either the untreated or the BAP groups. The above experiment confirmed that p53 and TSPfI can decrease the MCF7 tumor more than the p53 treated or the untreated groups.

EXAMPLE 6

$4 \times 10^5$ MCF7 cells were injected bilaterally into the mammary fat pads of the 28 nude mice. After two weeks of growth, these mice were randomly divided into four groups: 1)empty vector, 2) p53, 3) p53+TSPf, and 4) untreated. The mice received one injection of 200 pmoles of liposomes complexed with 14 ugs of DNA, and the tumors from the various treatment groups were measured 10 days after the treatment. The results are shown in Table 6 below.

TABLE 6

| Putative Anti-tumor Genes | Tumor Size (mm³) |
| --- | --- |
| Empty vector- | 54.7 ± 4.0 |
| p53 | 45.5 ± 5.0 |
| p53 + TSPf | 33.9 ± 3.6* |
| Untreated | 61.9 ± 8.3 |

*, p53 + TSPf vs Untreated, $p < .025$

As shown in Table 6 and previous tables, the additional reduction of the tumor by the combined use of p53 and TSPf compared to the use of p53 only, suggests that TSPf and p53 have different mechanisms of action. Although this does not preclude that the target of p53 is the vasculature of the tumor, the mechanism of inhibition of the tumor by p53 is uncertain at present. However, any mechanism of tumor inhibition by p53 and/or thrombospondin I must account for the low transfection efficiency of the tumor. Using a liposome completed to a chloramphenicol acetyltransferase marker, it has been demonstrated that less than 5% of the tumor derived from MDA-MB-435 cells was transfected with the marker gene, and assuming similar transfection efficiency here, these favorable results were observed notwithstanding the very low level of transfection.

EXAMPLE 7

In a further experiment, it was determined that liposomes complexed to DNA encoding the laminin peptide can inhibit tumor growth. More specifically, after administering the anesthetic, Metofane, to 24 female athymic nude mice, the mice were injected with $3.0 \times 10^5$ MDA-MB-435 tumor cells into the mammary fat pad using a stepper and a 27.5 g needle. Two weeks later, the mice whose tumors grew were divided into various treatment regimens, 8 mice per each regimen. The treatment regimens were as follows: (1) BAP, (2) laminin, and (3) p53+laminin. The mice were injected intravenously with 200 pmols of the liposomes complexed with 12.5 µgs of total DNA 6.25 µg of each vector when a combination was used. the mice then received 3 injections, each 10 days apart. The tumors were measured at the time of each injection and at the time of the last injection. The results are shown in Table 7 below.

TABLE 7

| Putative Anti-tumor Genes | Tumor Size (mm³) |
| --- | --- |
| BAP | 345 ± 23.5 |
| Laminin peptide | 280 ± 32.4 |
| Laminin peptide + p53 | 192 ± 10.5* |

*BAP vs. Laminin peptide + p53, $p < 0.05$

As shown in Table 7 above, cationic liposomes containing a combination of DNAs encoding laminin peptide+p53 were more effective in reducing tumor growth than when DNA encoding the anti-angiogenic peptide was used alone. Thus, the addition of a tumor suppressor gene, p53, can enhance the anti-tumor effect of the anti-angiogenic peptide.

EXAMPLE 8

Although intravenous injection is preferred, the method of administration of the liposome:DNA complex is not critical. It has been found that intratumoral injections are effective. In an experiment involving intratumoral injection, 18 mice were injected with $3 \times 10^5$ C6 glioma cells (rat brain tumors) subcutaneously. Six days after the injections, the mice were separated into 3 groups: 1) BAP, 2)FLK-DN (a dominant negative receptor), and 3) angiostatin. After the second intratumoral injection, there was a statistical difference between the angiostatin and the BAP groups. See FIG. 1. Thus, the therapy of the invention is effective when complexes are administered intratumorally. The therapy is effective against tumors other than breast tumors.

EXAMPLE 9

It was also found that a liposome: secretory angiostatin construct can be more effective than the non-secreted analog. In this experiment, 24 nude mice were injected with $3 \times 10^5$ MDA-MB-435 cells. Two weeks later the mice were divided into three groups, and received the following therapies intravenously:1) liposome:BAP, 2)liposome:secreted angiostatin, and 3)liposome:angiostatin. The concentration of DNA injected into the mice was 14.5 ugs. The mice received one injection of the liposome:DNA complex and their tumors were measured 10 days after the injection.

TABLE 8

Efficacy of Secretory Angiostatin

| Therapeutic DNA | Tumor Size (mm³) |
| --- | --- |
| Angiostatin | 28.8 ± 2.2 |
| Angiostatin-Secretory | 18.6 ± 1.8* |
| BAP | 30.5 ± 3.3 |

*, $P < 0.05$, BAP vs. Angiostatin-secretory

As seen in table 8, the secretory angiostatin treatment group was more effective than the vector control or the angiostatin treatment group in reducing the size of the tumor. From this experiment, it is demonstrated that a secretory sequence inserted into the 5' portion of the antiangiogenic inhibitor can increase its efficacy.

EXAMPLE 10

Further experiments indicate that cationic polymers can be useful as carriers in the present therapy, and can be the carriers of choice under certain conditions.

In the following example, a cationic polymer (Superfect) was compared to cationic liposomes as carrier for transfecting endothelial cells in vitro with the CAT marker. The cationic liposomes used for comparison to the polymer were DOSPER (Boerhinger), which of 14 lipids screened in vitro gave the best results. In this experiment, $1 \times 10^6$ Huvec cells were placed into each well of a 6 well plate. 25 uls of Superfect complexed with 2 ugs of DNA was added to each plate 24 hours after the initial seeding of the cells, and compared to plates to which had been added 2 ugs of DNA complexed with cationic liposomes. 36 hours after the transfection, the cells were lysed and the amount of CAT protein was assayed. The results are shown in Table 9.

TABLE 9

| Vectors | Activity (DPMS/protein) |
| --- | --- |
| Cationic liposomes with BAP | 31.1 ± 7.2 |
| Cationic liposomes with CAT | 682 ± 129 |
| Superfect with BAP | 21.4 ± 0.458 |
| Superfect with CAT | 10816 ± 687* |

$p < 0.001$, Superfect-CAt vs. Cationic liposome-CAT

This experiment suggests that a cationic polymer are superior in the transfection of endothelial cells, which is significant since we have hypothesized that endothelial cells of the tumor are a primary target of the therapeutic gene. Similarly, it has been found in some cell lines that Superfect is a better transfection agent in vitro than cationic liposomes.

EXAMPLE 11

Since Superfect appeared to be superior to cationic liposomes in the transfection of endothelial cells in vitro, it was investigated whether Superfect complexed to a therapeutic gene would inhibit tumor growth compared to the corresponding liposome complex. This experiment was based on the hypothesis that the endothelial cells and not other cells are the primary target of these cationic vehicle:DNA complexes. In this experiment, six mice were injected with $2.5 \times 10^5$ MDA cells into the mammary fat pad bilaterally. These tumors were allowed to grow to a large size for 2 months. At this size, the tumor growth is rapidly increasing at an exponential rate and is more resistant to treatment compared to smaller tumors. The mice were treated intravenously via the tail vein with either the cationic liposome:BAP-p53/CMV-TSPf or Superfect:BAP-p53/CMV-TSPf. 9.5 μgs of DNA were complexed to Supefect (108 μg) or the cationic liposome (200 pmoles). The mice received only one dose of these therapies and their tumors were measured 10 days later. The mice tolerated both therapies without any apparent toxicity. The results are given in the table below.

TABLE 10

| | Liposome | Superfect |
| --- | --- | --- |
| Before Treatment | 380 ± 95# | 384 ± 86 |
| After Treatment | 525 ± 80 | 403 ± 72 |

- tumor size in mm³

The Superfect carrier appears to be superior to the liposome carrier even after one dose in these large tumors. There was only a minimal increase (5%) in the Superfect-treated group whereas there was a marked increase in the liposome-treated group (38%). When the growth of individual tumors were examined and compared to pre-treatment measurements, all 6 tumors in the liposome-treated group increased in their size. In contrast, 4 of the 6 tumors in the Superfect group showed regression in their size compared to pre-treatment measurements.

EXAMPLE 12

This experiment was carried out using concatamer DNA encoding anti-angiogenic peptides. Mice injected with MDA-MB-435 tumor cells were treated as follows:

(1) BAP vector; (2) laminin peptide concatamer alone; and (3) laminin peptide vector alone. The mice received 2 intravenous injections, the first injection being 10 days after the malignant cells had been implanted into the mice, and the second injection 10 days later. The injections consisted of 200 pmols of liposomes completed with 12.5 μg of vector DNA. The results are shown in Table 11 below.

TABLE 11

| Putative Anti-tumor DNA | Tumor Size (mm³) |
| --- | --- |
| BAP | 86.8 ± 12.0 |
| Laminin peptide concatamer | 63.9 ± 4.8 |
| Laminin peptide | 53.7 ± 3.0* |

*Laminin peptide v. BAP, $p < 0.05$

As shown in Table 11, complexes containing DNA encoding laminin concatamer or laminin peptide reduced tumor growth compared to the control (BAP vector).

EXAMPLE 13

To assess efficacy using a combination of DNAs encoding antiangiogenic peptides, mice injected with MDA-MB-435 tumor cells were treated as follows:

(1) BAP vector; (2) TSPf vector+angiostatin vector; (3) laminin peptide vector+TSPf vector; (4) laminin peptide vector+angiostatin vector; and (5) laminin peptide and FlK-DN receptor. The mice received 5 intravenous injections, the first injection being 10 days after the malignant cells had been implanted into the mice, and the remaining injections 10 days apart. The injections consisted of 200 pmols of liposomes completed with 12.5 μg of total vector DNA, with 6.25 μg of each vector when a combination was used. The results are shown in Table 12 below.

TABLE 12

| Putative anti-tumor DNA | Tumor Size (mm³) |
| --- | --- |
| BAP | 626 ± 78 |
| TSPf + Angiostatin | 296 ± 40* |
| Laminin peptide + TSPf | 461 ± 54 |
| Laminin peptide + Angiostatin | 483 ± 46 |
| Laminin Peptide and F1K-DN | 482 ± 21 |

*TSPf + Angiostatin vs. BAP, $p < 0.01$

As shown in Table 12, cationic liposomes containing combinations of DNA encoding anti-angiogenic peptides showed favorable inhibition of tumor growth.

While the invention has been described in detail and by reference to specific embodiments thereof, it will be apparent to one of ordinary skill in the art that various changes and modifications can be made therein without departing from the spirit and scope thereof. Documents cited herein are incorporated by reference to the extent relevant to practicing the invention.

What is claimed is:

1. A method for inhibiting tumor growth in a subject bearing a tumor, which comprises injection of DNA encoding at least one anti-angiogenic protein or peptide provided with a carrier selected from the group consisting of liposomes, micelles and cationic polymer carriers, whereby said DNA is expressed and tumor growth is inhibited.

2. The method of claim 1, wherein the injection is intravenous injection.

3. The method of claim 1, wherein the carrier is a liposome.

4. The method of claim 1, wherein the carrier is a cationic polymer.

5. The method of claim 1, wherein the carrier is a micelle.

6. The method of claim 1, wherein the DNA is selected from the group consisting of those shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 31, SEQ ID NO: 35, and SEQ ID NO: 37.

7. The method of claim 1, wherein the DNA encodes a protein or peptide of thrombospondin I.

8. The method of claim 1, wherein the DNA encodes a protein or peptide of fibronectin.

9. The method of claim 1, wherein the DNA encodes a protein or peptide of laminin.

10. The method of claim 1, wherein the DNA encodes a protein or peptide of platelet factor 4.

11. The method of claim 1, wherein the DNA encodes a protein or peptide of angiostatin.

12. The method of claim 1, wherein the DNA encodes a protein or peptide of endostatin.

13. The method of claim 1, wherein the DNA encodes a protein or peptide of prolactin.

14. The method of claim 1, wherein the DNA encodes a protein or peptide of FlK-1-DN.

15. The method of claim 1, wherein the DNA is provided with a secretory signal.

16. A method for inhibiting tumor growth in a subject bearing a tumor, which comprises injection of DNA encoding at least one anti-angiogenic protein or peptide and DNA encoding a tumor suppressor protein, wherein the DNA is provided with a carrier selected from the group consisting of liposomes, micelles and cationic polymer carriers, whereby said DNA is expressed and tumor growth is inhibited.

17. The method of claim 16, wherein the DNA encoding a tumor suppressor protein encodes p53.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
       (A) LENGTH: 218 amino acids
       (B) TYPE: amino acid
       (D) TOPOLOGY: linear (xi) SEQUENCE DESCRIPTION: SEQ ID NO:1:

Met Thr Glu Glu Asn Lys Glu Leu Ala Asn Glu Leu Arg Arg Pro Pro
1               5                   10                  15

Leu Cys Tyr His Asn Gly Val Gln Tyr Arg Asn Asn Glu Glu Trp Thr
            20                  25                  30

Val Asp Ser Cys Thr Glu Cys His Cys Gln Asn Ser Val Thr Ile Cys
        35                  40                  45

Lys Lys Val Ser Cys Pro Ile Met Pro Cys Ser Asn Ala Thr Val Pro
    50                  55                  60

Asp Gly Glu Cys Cys Pro Arg Cys Trp Pro Ser Asp Ser Ala Asp Asp
65                  70                  75                  80

Gly Trp Ser Pro Trp Ser Glu Trp Thr Ser Cys Ser Thr Ser Cys Gly
                85                  90                  95

Asn Gly Ile Gln Gln Arg Gly Arg Ser Cys Asp Ser Leu Asn Asn Arg
            100                 105                 110

Cys Glu Gly Ser Ser Val Gln Thr Arg Thr Cys His Ile Gln Glu Cys
        115                 120                 125

Asp Lys Arg Phe Lys Gln Asp Gly Gly Trp Ser His Trp Ser Pro Trp
    130                 135                 140

Ser Ser Cys Ser Val Thr Cys Gly Asp Gly Val Ile Thr Arg Ile Thr
145                 150                 155                 160

Asn Leu Cys Ser Pro Ser Pro Gln Met Asn Gly Lys Pro Cys Glu Gly
                165                 170                 175

Arg Glu Ala Glu Thr Lys Ala Cys Lys Lys Asp Ala Cys Pro Ile Asn
            180                 185                 190

Gly Gly Trp Gly Pro Trp Ser Pro Trp Asp Ile Cys Ser Val Thr Cys
        195                 200                 205

Gly Gly Gly Val Gln Lys Arg Ser Arg Leu
    210                 215

(2) INFORMATION FOR SEQ ID NO:2:

(i) SEQUENCE CHARACTERISTICS:
       (A) LENGTH: 657 base pairs
       (B) TYPE: nucleic acid
       (C) STRANDEDNESS: single
       (D) TOPOLOGY: linear (xi) SEQUENCE DESCRIPTION: SEQ ID NO:2:

ATGACTGAAG AGAACAAAGA GTTGGCCAAT GAGCTGAGGC GGCCTCCCCT ATGCTATCAC      60

AACGGAGTTC AGTACAGAAA TAACGAGGAA TGGACTGTTG ATAGCTGCAC TGAGTGTCAC     120

TGTCAGAACT CAGTTACCAT CTGCAAAAAG GTGTCCTGCC CCATCATGCC CTGCTCCAAT     180

GCCACAGTTC CTGATGGAGA ATGCTGTCCT CGCTGTTGGC CCAGCGACTC TGCGGACGAT     240

GGCTGGTCTC CATGGTCCGA GTGGACCTCC TGTTCTACGA GCTGTGGCAA TGGAATTCAG     300

```
CAGCGCGGCC GCTCCTGCGA TAGCCTCAAC AACCGATGTG AGGGCTCCTC GGTCCAGACA      360

CGGACCTGCC ACATTCAGGA GTGTGACAAA AGATTTAAAC AGGATGGTGG CTGGAGCCAC      420

TGGTCCCCGT GGTCATCTTG TTCTGTGACA TGTGGTGATG GTGTGATCAC AAGGATCCGG      480

CTCTGCAACT CTCCCAGCCC CCAGATGAAT GGGAAACCCT GTGAAGGCGA AGCGCGGGAG      540

ACCAAAGCCT GCAAGAAAGA CGCCTGCCCC ATCAATGGAG CTGGGGTCC TTGGTCACCA       600

TGGGACATCT GTTCTGTCAC CTGTGGAGGA GGGGTACAGA AACGTAGTCG TCTCTAA         657
```

(2) INFORMATION FOR SEQ ID NO:3:

(i) SEQUENCE CHARACTERISTICS:
        (A) LENGTH: 441 amino acids
        (B) TYPE: amino acid
        (D) TOPOLOGY: linear (xi) SEQUENCE DESCRIPTION: SEQ ID NO:3:

```
Met Thr Glu Glu Asn Lys Glu Leu Ala Asn Glu Leu Arg Arg Pro Pro
1               5                   10                  15

Leu Cys Tyr His Asn Gly Val Gln Tyr Arg Asn Asn Glu Glu Trp Thr
            20                  25                  30

Asp Val Ser Cys Thr Glu Cys His Cys Gln Asn Ser Val Thr Ile Cys
        35                  40                  45

Lys Lys Val Ser Cys Pro Ile Met Pro Cys Ser Asn Ala Thr Val Pro
    50                  55                  60

Asp Gly Glu Cys Cys Pro Arg Cys Trp Pro Ser Asp Ser Ala Asp Asp
65                  70                  75                  80

Trp Gly Ser Pro Trp Ser Glu Trp Thr Ser Cys Ser Thr Ser Cys Gly
                85                  90                  95

Gly Asn Ile Gln Gln Arg Gly Arg Ser Cys Asp Ser Leu Asn Asn Arg
            100                 105                 110

Cys Glu Gly Ser Ser Val Gln Thr Arg Thr Cys His Ile Gln Glu Cys
        115                 120                 125

Asp Lys Arg Phe Lys Gln Asp Gly Gly Trp Ser His Trp Ser Pro Trp
    130                 135                 140

Ser Ser Cys Ser Val Thr Cys Gly Asp Gly Val Ile Thr Arg Ile Thr
145                 150                 155                 160

Leu Cys Asn Ser Pro Ser Pro Gln Met Asn Gly Lys Pro Cys Glu Gly
                165                 170                 175

Glu Ala Arg Glu Thr Lys Ala Cys Lys Lys Asp Ala Cys Pro Ile Asn
            180                 185                 190

Gly Gly Trp Gly Pro Trp Ser Pro Trp Asp Ile Cys Ser Val Thr Cys
        195                 200                 205

Gly Gly Gly Val Gln Lys Arg Ser Arg Leu Cys Val Asp Ser Arg Met
    210                 215                 220

Thr Glu Glu Asn Lys Glu Leu Ala Asn Glu Leu Arg Arg Pro Pro Leu
225                 230                 235                 240

Cys Tyr His Asn Gly Val Gln Tyr Arg Asn Asn Glu Glu Trp Thr Val
                245                 250                 255

Asp Ser Cys Thr Glu Cys His Cys Gln Asn Ser Val Thr Ile Cys Lys
            260                 265                 270

Lys Val Ser Cys Pro Ile Met Pro Cys Ser Asn Ala Thr Val Pro Asp
        275                 280                 285

Gly Glu Cys Cys Pro Arg Cys Trp Pro Ser Asp Ser Ala Asp Asp Gly
    290                 295                 300
```

```
Trp Ser Pro Trp Ser Glu Trp Thr Ser Cys Ser Thr Ser Cys Gly Asn
305                 310                 315                 320

Gly Ile Gln Gln Arg Gly Arg Ser Cys Asp Ser Leu Asn Asn Arg Cys
                325                 330                 335

Glu Gly Ser Ser Val Gln Thr Arg Thr Cys His Ile Gln Glu Cys Asp
            340                 345                 350

Lys Arg Phe Lys Gln Asp Gly Gly Trp Ser His Trp Ser Pro Trp Ser
        355                 360                 365

Ser Cys Ser Val Thr Cys Gly Asp Gly Val Ile Thr Arg Ile Thr Leu
    370                 375                 380

Cys Asn Ser Pro Ser Pro Gln Met Asn Gly Lys Pro Cys Glu Gly Glu
385                 390                 395                 400

Ala Arg Glu Thr Lys Ala Cys Lys Lys Asp Ala Cys Pro Ile Asn Gly
                405                 410                 415

Gly Trp Gly Pro Trp Ser Pro Trp Asp Ile Cys Ser Val Thr Cys Gly
                420                 425                 430

Gly Gly Val Gln Lys Arg Ser Arg Leu
            435                 440

(2) INFORMATION FOR SEQ ID NO:4:

(i) SEQUENCE CHARACTERISTICS:
        (A) LENGTH: 1326 base pairs
        (B) TYPE: nucleic acid
        (C) STRANDEDNESS: single
        (D) TOPOLOGY: linear (xi) SEQUENCE DESCRIPTION: SEQ ID NO:4:

ATGACTGAAG AGAACAAAGA GTTGGCCAAT GAGCTGAGGC GGCCTCCCCT ATGCTATCAC      60

AACGGAGTTC AGTACAGAAA TAACGAGGAA TGGACTGTTG ATAGCTGCAC TGAGTGTCAC     120

TGTCAGAACT CAGTTACCAT CTGCAAAAAG GTGTCCTGCC CCATCATGCC CTGCTCCAAT     180

GCCACAGTTC CTGATGGAGA ATGCTGTCCT CGCTGTTGGC CCAGCGACTC TGCGGACGAT     240

GGCTGGTCTC CATGGTCCGA GTGGACCTCC TGTTCTACGA GCTGTGGCAA TGGAATTCAG     300

CAGCGCGGCC GCTCCTGCGA TAGCCTCAAC AACCGATGTG AGGGCTCCTC GGTCCAGACA     360

CGGACCTGCC ACATTCAGGA GTGTGACAAA AGATTTAAAC AGGATGGTGG CTGGAGCCAC     420

TGGTCCCCGT GGTCATCTTG TTCTGTGACA TGTGGTGATG GTGTGATCAC AAGGATCCGG     480

CTCTGCAACT CTCCCAGCCC CCAGATGAAT GGGAAACCCT GTGAAGGCGA AGCGCGGGAG     540

ACCAAAGCCT GCAAGAAAGA CGCCTGCCCC ATCAATGGAG GCTGGGGTCC TTGGTCACCA     600

TGGGACATCT GTTCTGTCAC CTGTGGAGGA GGGGTACAGA AACGTAGTCG TCTCTGCGTC     660

GACTCTAGAA TGACTGAAGA GAACAAAGAG TTGGCCAATG AGCTGAGGCG GCCTCCCCTA     720

TGCTATCACA ACGGAGTTCA GTACAGAAAT AACGAGGAAT GGACTGTTGA TAGCTGCACT     780

GAGTGTCACT GTCAGAACTC AGTTACCATC TGCAAAAAGG TGTCCTGCCC CATCATGCCC     840

TGCTCCAATG CCACAGTTCC TGATGGAGAA TGCTGTCCTC GCTGTTGGCC CAGCGACTCT     900

GCGGACGATG GCTGGTCTCC ATGGTCCGAG TGGACCTCCT GTTCTACGAG CTGTGGCAAT     960

GGAATTCAGC AGCGCGGCCG CTCCTGCGAT AGCCTCAACA ACCGATGTGA GGGCTCCTCG    1020

GTCCAGACAC GGACCTGCCA CATTCAGGAG TGTGACAAAA GATTTAAACA GGATGGTGGC    1080

TGGAGCCACT GGTCCCCGTG GTCATCTTGT TCTGTGACAT GTGGTGATGG TGTGATCACA    1140

AGGATCCGGC TCTGCAACTC TCCCAGCCCC CAGATGAATG GGAAACCCTG TGAAGGCGAA    1200
```

```
GCGCGGGAGA CCAAAGCCTG CAAGAAAGAC GCCTGCCCCA TCAATGGAGG CTGGGGTCCT      1260

TGGTCACCAT GGGACATCTG TTCTGTCACC TGTGGAGGAG GGGTACAGAA ACGTAGTCGT      1320

CTCTAA                                                                1326

(2) INFORMATION FOR SEQ ID NO:5:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:5:

Met Tyr Ile Gly Ser Arg
1               5

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:6:

GTCGACATGT ATATTGGTTC TCGTTAAGTC GAC                                   33

(2) INFORMATION FOR SEQ ID NO:7:

(i) SEQUENCE CHARACTERISTICS:
        (A) LENGTH: 25 amino acids
        (B) TYPE: amino acid
        (D) TOPOLOGY: linear (xi) SEQUENCE DESCRIPTION: SEQ ID NO:7:

Met Tyr Ile Gly Ser Arg Gly Lys Ser Tyr Ile Gly Ser Arg Gly Lys
1               5                   10                  15

Ser Tyr Ile Gly Ser Arg Gly Lys Ser
                20                  25

(2) INFORMATION FOR SEQ ID NO:8:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (xi) SEQUENCE DESCRIPTION: SEQ ID NO:8:

GTCGACATGT ATATTGGTTC TCGTGTAAAA GTTATATTGG TTCTCGTGGT AAAAGTTATA      60

TTGGTTCTCG TGGTAAAAGT TAAGTCGACC                                      90

(2) INFORMATION FOR SEQ ID NO:9:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:9:

Met Leu Tyr Lys Lys Ile Ile Lys Lys Leu Leu Glu Ser
1               5                   10

(2) INFORMATION FOR SEQ ID NO:10:
```

```
    (i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:10:

GTCGACATGC TTTATAAGAA GATCATCAAG AAGCTTCTTG AGAGTTAAGT CGAC          54

(2) INFORMATION FOR SEQ ID NO:11:

(i) SEQUENCE CHARACTERISTICS:
        (A) LENGTH: 46 amino acids
        (B) TYPE: amino acid
        (D) TOPOLOGY: linear (xi) SEQUENCE DESCRIPTION: SEQ ID NO:11:

Met Leu Tyr Lys Lys Ile Ile Lys Lys Leu Leu Glu Ser Gly Lys Ser
1               5                  10                  15

Leu Tyr Lys Lys Ile Ile Lys Lys Leu Leu Glu Ser Gly Lys Ser Leu
               20                  25                  30

Tyr Lys Lys Ile Ile Lys Lys Leu Leu Glu Ser Gly Lys Ser
           35                  40                  45

(2) INFORMATION FOR SEQ ID NO:12:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (xi) SEQUENCE DESCRIPTION: SEQ ID NO:12:

GTCGACATGC TTTATAAGAA GATCATCAAG AAGCTTCTTG AGAGTGGTAA AAGTCTTTAT    60

AAGAAGATCA TCAAGAAGCT TCTTGAGAGT GGTAAAAGTC TTTATAAGAA GATCATCAAG   120

AAGCTTCTTG AGAGTGGTAA AAGTTAAGTC GAC                                153

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:13:

Met Phe Cys Tyr Trp Lys Val Cys Trp
1               5

(2) INFORMATION FOR SEQ ID NO:14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:14:

GTCGACATGT TCTGTTATTG GAAGGTTTGT TGGTAAGTCG AC                       42

(2) INFORMATION FOR SEQ ID NO:15:

(i) SEQUENCE CHARACTERISTICS:
        (A) LENGTH: 34 amino acids
        (B) TYPE: amino acid
        (D) TOPOLOGY: linear
```

(xi) SEQUENCE DESCRIPTION: SEQ ID NO:15:

Met Phe Cys Tyr Trp Lys Val Cys Trp Gly Lys Ser Phe Cys Tyr Trp
1               5                   10                  15

Lys Val Cys Trp Gly Lys Ser Phe Cys Tyr Trp Lys Val Cys Trp Gly
                20                  25                  30

Lys Ser (2) INFORMATION FOR SEQ ID NO:16:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (xi) SEQUENCE DESCRIPTION: SEQ ID NO:16:

GTCGACATGT TCTGTTATTG GAAGGTTTGT TGGGGTAAAA GTTTCTGTTA TTGGAAGGTT     60

TGTTGGGGTA AAAGTTTCTG TTATTGGAAG GTTTGTTGGG GTAAAAGTTA AGTCGAC      117

(2) INFORMATION FOR SEQ ID NO:17:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:17:

Met Gly Arg Gly Asp
1               5

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:18:

GTCGACATGG GTCGTGGTGA TTAAGTCGAC                                      30

(2) INFORMATION FOR SEQ ID NO:19:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:19:

Met Gly Arg Gly Asp Gly Lys Ser Gly Arg Gly Asp Gly Lys Ser Gly
1               5                   10                  15

Arg Gly Asp Gly Lys Ser
                20

(2) INFORMATION FOR SEQ ID NO:20:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:20:

```
GTCGACATGG GTCGTGGTGA TGGTAAAAGT GGTCGTGGTG ATGGTAAAAG TGGTCGTGGT    60

GATGGTAAAA GTTAAGTCGA C                                              81
```

(2) INFORMATION FOR SEQ ID NO:21:

(i) SEQUENCE CHARACTERISTICS:
        (A) LENGTH: 210 amino acids
        (B) TYPE: amino acid
        (D) TOPOLOGY: linear (xi) SEQUENCE DESCRIPTION: SEQ ID NO:21:

```
Met Val Tyr Leu Ser Glu Cys Lys Thr Gly Ile Gly Asn Gly Tyr Arg
 1               5                  10                  15

Gly Thr Met Ser Arg Thr Lys Ser Gly Val Ala Cys Gln Lys Trp Gly
                20                  25                  30

Ala Thr Phe Pro His Val Pro Asn Tyr Ser Pro Ser Thr His Pro Asn
            35                  40                  45

Glu Gly Leu Glu Glu Asn Tyr Cys Arg Asn Pro Asp Asn Asp Glu Gln
        50                  55                  60

Gly Pro Trp Cys Tyr Thr Thr Asp Pro Asp Lys Arg Tyr Asp Tyr Cys
65                  70                  75                  80

Asn Ile Pro Glu Cys Glu Glu Cys Met Tyr Cys Ser Gly Glu Lys
                85                  90                  95

Tyr Glu Gly Lys Ile Ser Lys Thr Met Ser Gly Lys Asp Cys Gln Ala
                100                 105                 110

Trp Asp Ser Gln Ser Pro His Ala His Gly Tyr Ile Pro Ala Lys Phe
            115                 120                 125

Pro Ser Lys Asn Leu Lys Met Asn Tyr Cys His Asn Pro Asp Gly Glu
        130                 135                 140

Pro Arg Pro Trp Cys Phe Thr Thr Asp Pro Thr Lys Arg Trp Glu Tyr
145                 150                 155                 160

Cys Asp Ile Pro Arg Cys Thr Thr Pro Pro Pro Pro Ser Pro Thr
                165                 170                 175

Tyr Gln Cys Leu Lys Gly Arg Gly Glu Asn Tyr Arg Gly Thr Val Ser
            180                 185                 190

Val Thr Val Ser Gly Lys Thr Cys Gln Arg Trp Ser Glu Gln Thr Pro
            195                 200                 205

His Arg
    210
```

(2) INFORMATION FOR SEQ ID NO:22:

(i) SEQUENCE CHARACTERISTICS:
        (A) LENGTH: 645 base pairs
        (B) TYPE: nucleic acid
        (C) STRANDEDNESS: single
        (D) TOPOLOGY: linear (xi) SEQUENCE DESCRIPTION: SEQ ID NO:22:

```
GTCGACATGG TGTATCTGTC AGAATGTAAG ACCGGCATCG GCAACGGCTA CAGAGGAACC    60

ATGTCCAGGA CAAAGAGTGG TGTTGCCTGT CAAAAGTGGG GTGCCACGTT CCCCCACGTA   120

CCCAACTACT CTCCCAGTAC ACATCCCAAT GAGGGACTAG AAGAGAACTA CTGTAGGAAC   180

CCAGACAATG ATGAACAAGG GCCTTGGTGC TACACTACAG ATCCGGACAA GAGATATGAC   240

TACTGCAACA TTCCTGAATG TGAAGAGGAA TGCATGTACT GCAGTGGAGA AAAGTATGAG   300

GGCAAAATCT CCAAGACCAT GTCTGGACTT GACTGCCAGG CCTGGGATTC TCAGAGCCCA   360
```

-continued

```
CATGCTCATG GATACATCCC TGCCAAATTT CCAAGCAAGA ACCTGAAGAT GAATTATTGC      420

CACAACCCTG ACGGGAGCC AAGGCCCTGG TGCTTCACAA CAGACCCCAC CAAACGCTGG       480

GAATACTGTG ACATCCCCCG CTGCACAACA CCCCCGCCCC CACCCAGCCC AACCTACCAA      540

TGTCTGAAAG GAAGAGGTGA AAATTACCGA GGGACCGTGT CTGTCACCGT GTCTGGGAAA     600

ACCTGTCAGC GCTGGAGTGA GCAAACCCCT CATAGGTGAG TCGAC                    645
```

(2) INFORMATION FOR SEQ ID NO:23:

(i) SEQUENCE CHARACTERISTICS:
        (A) LENGTH: 423 amino acids
        (B) TYPE: amino acid
        (D) TOPOLOGY: linear (xi) SEQUENCE DESCRIPTION: SEQ ID NO:23:

```
Met Val Tyr Leu Ser Glu Cys Lys Thr Gly Ile Gly Asn Gly Tyr Arg
 1               5                  10                  15

Gly Thr Met Ser Arg Thr Lys Ser Gly Val Ala Cys Gln Lys Trp Gly
                20                  25                  30

Ala Thr Phe Pro His Val Pro Asn Tyr Ser Pro Ser Thr His Pro Asn
            35                  40                  45

Glu Gly Leu Glu Glu Asn Tyr Cys Arg Asn Pro Asp Asn Asp Glu Gln
        50                  55                  60

Gly Pro Trp Cys Tyr Thr Thr Asp Pro Asp Lys Arg Tyr Asp Tyr Cys
65                  70                  75                  80

Asn Ile Pro Glu Cys Glu Glu Glu Cys Met Tyr Cys Ser Gly Glu Lys
                85                  90                  95

Tyr Glu Gly Lys Ile Ser Lys Thr Met Ser Gly Lys Asp Cys Gln Ala
               100                 105                 110

Trp Asp Ser Gln Ser Pro His Ala His Gly Tyr Ile Pro Ala Lys Phe
           115                 120                 125

Pro Ser Lys Asn Leu Lys Met Asn Tyr Cys His Asn Pro Asp Gly Glu
       130                 135                 140

Pro Arg Pro Trp Cys Phe Thr Thr Asp Pro Thr Lys Arg Trp Glu Tyr
145                 150                 155                 160

Cys Asp Ile Pro Arg Cys Thr Thr Pro Pro Pro Pro Ser Pro Thr
               165                 170                 175

Tyr Gln Cys Leu Lys Gly Arg Gly Glu Asn Tyr Arg Gly Thr Val Ser
           180                 185                 190

Val Thr Val Ser Gly Lys Thr Cys Gln Arg Trp Ser Glu Gln Thr Pro
       195                 200                 205

His Arg Gly Lys Ser Met Val Tyr Leu Ser Glu Cys Lys Thr Gly Ile
   210                 215                 220

Gly Asn Gly Tyr Arg Gly Thr Met Ser Arg Thr Lys Ser Gly Val Ala
225                 230                 235                 240

Cys Gln Lys Trp Gly Ala Thr Phe Pro His Val Pro Asn Tyr Ser Pro
               245                 250                 255

Ser Thr His Pro Asn Glu Gly Leu Glu Glu Asn Tyr Cys Arg Asn Pro
           260                 265                 270

Asp Asn Asp Glu Gln Gly Pro Trp Cys Tyr Thr Thr Asp Pro Asp Lys
       275                 280                 285

Arg Tyr Asp Tyr Cys Asn Ile Pro Glu Cys Glu Glu Glu Cys Met Tyr
   290                 295                 300

Cys Ser Gly Glu Lys Tyr Glu Gly Lys Ile Ser Lys Thr Met Ser Gly
305                 310                 315                 320
```

```
Lys Asp Cys Gln Ala Trp Asp Ser Gln Ser Pro His Ala His Gly Tyr
            325                 330                 335

Ile Pro Ala Lys Phe Pro Ser Lys Asn Leu Lys Met Asn Tyr Cys His
        340                 345                 350

Asn Pro Asp Gly Glu Pro Arg Pro Trp Cys Phe Thr Thr Asp Pro Thr
            355                 360                 365

Lys Arg Trp Glu Tyr Cys Asp Ile Pro Arg Cys Thr Thr Pro Pro Pro
    370                 375                 380

Pro Pro Ser Pro Thr Tyr Gln Cys Leu Lys Gly Arg Gly Glu Asn Tyr
385                 390                 395                 400

Arg Gly Thr Val Ser Val Thr Val Ser Gly Lys Thr Cys Gln Arg Trp
                405                 410                 415

Ser Glu Gln Thr Pro His Arg
            420
```

(2) INFORMATION FOR SEQ ID NO:24:

(i) SEQUENCE CHARACTERISTICS:
        (A) LENGTH: 1284 base pairs
        (B) TYPE: nucleic acid
        (C) STRANDEDNESS: single
        (D) TOPOLOGY: linear (xi) SEQUENCE DESCRIPTION: SEQ ID NO:24:

```
GTCGACATGG TGTATCTGTC AGAATGTAAG ACCGGCATCG GCAACGGCTA CAGAGGAACC    60

ATGTCCAGGA CAAAGAGTGG TGTTGCCTGT CAAAAGTGGG GTGCCACGTT CCCCCACGTA   120

CCCAACTACT CTCCCAGTAC ACATCCCAAT GAGGGACTAG AAGAGAACTA CTGTAGGAAC   180

CCAGACAATG ATGAACAAGG GCCTTGGTGC TACACTACAG ATCCGGACAA GAGATATGAC   240

TACTGCAACA TTCCTGAATG TGAAGAGGAA TGCATGTACT GCAGTGGAGA AAAGTATGAG   300

GGCAAAATCT CCAAGACCAT GTCTGGACTT GACTGCCAGG CCTGGGATTC TCAGAGCCCA   360

CATGCTCATG GATACATCCC TGCCAAATTT CCAAGCAAGA ACCTGAAGAT GAATTATTGC   420

CACAACCCTG ACGGGGAGCC AAGGCCCTGG TGCTTCACAA CAGACCCCAC CAAACGCTGG   480

GAATACTGTG ACATCCCCCG CTGCACAACA CCCCCGCCCC CACCCAGCCC AACCTACCAA   540

TGTCTGAAAG GAAGAGGTGA AAATTACCGA GGACCGTGTC TGTCACCGT GTCTGGGAAA   600

ACCTGTCAGC GCTGGAGTGA GCAAACCCCT CATAGGGGTA AAAGTATGGT GTATCTGTCA   660

GAATGTAAGA CCGGCATCGG CAACGGCTAC AGAGGAACCA TGTCCAGGAC AAAGAGTGGT   720

GTTGCCTGTC AAAAGTGGGG TGCCACGTTC CCCCACGTAC CCAACTACTC TCCCAGTACA   780

CATCCCAATG AGGGACTAGA AGAGAACTAC TGTAGGAACC CAGACAATGA TGAACAAGGG   840

CCTTGGTGCT ACACTACAGA TCCGGACAAG AGATATGACT ACTGCAACAT TCCTGAATGT   900

GAAGAGGAAT GCATGTACTG CAGTGGAGAA AAGTATGAGG GCAAAATCTC CAAGACCATG   960

TCTGGACTTG ACTGCCAGGC CTGGGATTCT CAGAGCCCAC ATGCTCATGG ATACATCCCT  1020

GCCAAATTTC CAAGCAAGAA CCTGAAGATG AATTATTGCC ACAACCCTGA CGGGGAGCCA  1080

AGGCCCTGGT GCTTCACAAC AGACCCCACC AAACGCTGGG AATACTGTGA CATCCCCCGC  1140

TGCACAACAC CCCCGCCCCC ACCCAGCCCA ACCTACCAAT GTCTGAAAGG AAGAGGTGAA  1200

AATTACCGAG GACCGTGTCT GTCACCGTG TCTGGGAAAA CCTGTCAGCG CTGGAGTGAG  1260

CAAACCCCTC ATAGGTGAGT CGAC                                        1284
```

(2) INFORMATION FOR SEQ ID NO:25:

(i) SEQUENCE CHARACTERISTICS:
        (A) LENGTH: 125 amino acids
        (B) TYPE: amino acid
        (D) TOPOLOGY: linear (xi) SEQUENCE DESCRIPTION: SEQ ID NO:25:

Met Leu Pro Ile Cys Pro Gly Gly Ala Ala Arg Cys Gln Val Thr Leu
1               5                   10                  15

Arg Glu Leu Phe Asp Arg Ala Val Val Leu Ser His Tyr Ile His Asn
                20                  25                  30

Leu Ser Ser Glu Met Phe Ser Glu Phe Glu Lys Arg Tyr Thr His Gly
            35                  40                  45

Arg Gly Phe Ile Thr Lys Ala Ile Asn Ser Cys His Thr Ser Ser Leu
        50                  55                  60

Ala Thr Pro Glu Asp Lys Glu Gln Ala Gln Gln Met Asn Gln Lys Asp
65                  70                  75                  80

Phe Leu Ser Leu Ile Val Ser Ile Leu Arg Ser Trp Asn Glu Pro Leu
                85                  90                  95

Tyr His Leu Val Thr Glu Val Arg Gly Met Gln Glu Ala Pro Gln Ala
                100                 105                 110

Ile Leu Ser Lys Ala Val Glu Ile Glu Glu Gln Thr Lys
            115                 120                 125

(2) INFORMATION FOR SEQ ID NO:26:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (xi) SEQUENCE DESCRIPTION: SEQ ID NO:26:

GTCGACATGT TGCCCATCTG TCCCGGCGGG GCTGCCCGAT GCCAGGTGAC CCTTCGAGAC      60

CTGTTTGACC GCGCCGTCGT CCTGTCCCAC TACATCCATA ACCTCTCCTC AGAAATGTTC     120

AGCGAATTCG ATAAACGGTA TACCCATGGC CGGGGGTTCA TTACCAAGGC CATCAACAGC    180

TGCCACACTT CTTCCCTTGC CACCCCCGAA GACAAGGAGC AAGCCCAACA GATGAATCAA    240

AAAGACTTTC TGAGCCTGAT AGTCAGCATA TTGCGATCCT GGAATGAGCC TCTGTATCAT    300

CTGGTCACGG AAGTACGTGG TATGCAAGAA GCCCCGGAGG CTATCCTATC CAAAGCTGTA    360

GAGATTGAGG AGCAAACCAA ATAAGTCGAC                                      390

(2) INFORMATION FOR SEQ ID NO:27:

(i) SEQUENCE CHARACTERISTICS:
        (A) LENGTH: 253 amino acids
        (B) TYPE: amino acid
        (D) TOPOLOGY: linear (xi) SEQUENCE DESCRIPTION: SEQ ID NO:27:

Met Leu Pro Ile Cys Pro Gly Gly Ala Ala Arg Cys Gln Val Thr Leu
1               5                   10                  15

Arg Glu Leu Phe Asp Arg Ala Val Val Leu Ser His Tyr Ile His Asn
                20                  25                  30

Leu Ser Ser Glu Met Phe Ser Glu Phe Glu Lys Arg Tyr Thr His Gly
            35                  40                  45

Arg Gly Phe Ile Thr Lys Ala Ile Asn Ser Cys His Thr Ser Ser Leu
        50                  55                  60

```
Ala Thr Pro Glu Asp Lys Glu Gln Ala Gln Gln Met Asn Gln Lys Asp
 65                  70                  75                  80

Phe Leu Ser Leu Ile Val Ser Ile Leu Arg Ser Trp Asn Glu Pro Leu
                 85                  90                  95

Tyr His Leu Val Thr Glu Val Arg Gly Met Gln Glu Ala Pro Gln Ala
            100                 105                 110

Ile Leu Ser Lys Ala Val Glu Ile Glu Glu Gln Thr Lys Gly Lys Ser
        115                 120                 125

Met Leu Pro Ile Cys Pro Gly Gly Ala Ala Arg Cys Gln Val Thr Leu
    130                 135                 140

Arg Glu Leu Phe Asp Arg Ala Val Val Leu Ser His Tyr Ile His Asn
145                 150                 155                 160

Leu Ser Ser Glu Met Phe Ser Glu Phe Lys Arg Tyr Thr His Gly
                165                 170                 175

Arg Gly Phe Ile Thr Lys Ala Ile Asn Ser Cys His Thr Ser Ser Leu
            180                 185                 190

Ala Thr Pro Glu Asp Lys Glu Gln Ala Gln Gln Met Asn Gln Lys Asp
        195                 200                 205

Phe Leu Ser Leu Ile Val Ser Ile Leu Arg Ser Trp Asn Glu Pro Leu
    210                 215                 220

Tyr His Leu Val Thr Glu Val Arg Gly Met Gln Glu Ala Pro Gln Ala
225                 230                 235                 240

Ile Leu Ser Lys Ala Val Glu Ile Glu Glu Gln Thr Lys
                245                 250
```

(2) INFORMATION FOR SEQ ID NO:28:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (xi) SEQUENCE DESCRIPTION: SEQ ID NO:28:

```
GTCGACATGT TGCCCATCTG TCCCGGCGGG GCTGCCCGAT GCCAGGTGAC CCTTCGAGAC    60

CTGTTTGACC GCGCCGTCGT CCTGTCCCAC TACATCCATA ACCTCTCCTC AGAAATGTTC   120

AGCGAATTCG ATAAACGGTA TACCCATGGC CGGGGGTTCA TTACCAAGGC CATCAACAGC   180

TGCCACACTT CTTCCCTTGC CACCCCCGAA GACAAGGAGC AAGCCCAACA GATGAATCAA   240

AAAGACTTTC TGAGCCTGAT AGTCAGCATA TTGCGATCCT GGAATGAGCC TCTGTATCAT   300

CTGGTCACGG AAGTACGTGG TATGCAAGAA GCCCCGGAGG CTATCCTATC CAAAGCTGTA   360

GAGATTGAGG AGCAAACCGG TAAAAGTATG TTGCCCATCT GTCCCGGCGG GGCTGCCCGA   420

TGCCAGGTGA CCCTTCGAGA CCTGTTTGAC CGCGCCGTCG TCCTGTCCCA CTACATCCAT   480

AACCTCTCCT CAGAAATGTT CAGCGAATTC GATAAACGGT ATACCCATGG CCGGGGGTTC   540

ATTACCAAGG CCATCAACAG CTGCCACACT TCTTCCCTTG CCACCCCCGA AGACAAGGAG   600

CAAGCCCAAC AGATGAATCA AAAAGACTTT CTGAGCCTGA TAGTCAGCAT ATTGCGATCC   660

TGGAATGAGC TCTGTATCA TCTGGTCACG GAAGTACGTG GTATGCAAGA AGCCCCGGAG   720

GCTATCCTAT CCAAAGCTGT AGAGATTGAG GAGCAAACCA ATAAGTCGA C             771
```

(2) INFORMATION FOR SEQ ID NO:29:

(i) SEQUENCE CHARACTERISTICS:
        (A) LENGTH: 161 base pairs
        (B) TYPE: nucleic acid (C) STRANDEDNESS: single
            (D) TOPOLOGY: linear (xi) SEQUENCE DESCRIPTION: SEQ ID NO:29:

ATGCTGAGGC GGCCTCCCCT ATGCTATCAC AACGGAGTTC AGTACAGAAA TAACGGTAAA      60

AGATCCCCGT GGTCATCTTG TTCTGTGACA TGTGGTGATG GTGTGATGGT AAAAGAAGTG     120

GTACCCTGTA GACAAGACAG TGGACACCTC CTCCCCATTA A                         161

(2) INFORMATION FOR SEQ ID NO:30:

(i) SEQUENCE CHARACTERISTICS:
        (A) LENGTH: 63 amino acids
        (B) TYPE: amino acid
        (D) TOPOLOGY: linear (xi) SEQUENCE DESCRIPTION: SEQ ID NO:30:

Met Leu Arg Arg Pro Pro Leu Cys Tyr His Asn Gly Val Gln Tyr Arg
1               5                  10                  15

Asn Asn Glu Glu Trp Thr Val Asp Ser Gly Lys Ser Ser Pro Trp Ser
            20                  25                  30

Ser Cys Ser Val Thr Cys Gly Asp Gly Val Ile Thr Arg Ile Gly Lys
        35                  40                  45

Ser Ser Pro Trp Asp Ile Cys Ser Val Thr Cys Gly Gly Gly Val
    50                  55                  60

(2) INFORMATION FOR SEQ ID NO:31:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (xi) SEQUENCE DESCRIPTION: SEQ ID NO:31:

ATGCTGAGGC GGCCTCCCCT ATGCTATCAC AACGGAGTTC AGTACAGAAA TAACGGTAAA      60

AGATCCCCGT GGTCATCTTG TTCTGTGACA TGTGGTGATG GTGTGATGGT AAAAGAAGTG     120

GTACCCTGTA GACAAGACAG TGGACACCTC CTCCCCATTA TATTGGTTCT CGTGGTAAAA     180

GATAA                                                                 185

(2) INFORMATION FOR SEQ ID NO:32:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:32:

TAGGTCTAGA ATGACTGAAG AGAACAAAGA G                                     31

(2) INFORMATION FOR SEQ ID NO:33:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:33:

ATGGTCTAGA TTAGAGACGA CTACGTTTCT G                                     31

-continued (2) INFORMATION FOR SEQ ID NO:34:

(i) SEQUENCE CHARACTERISTICS:
        (A) LENGTH: 805 amino acids
        (B) TYPE: amino acid
        (D) TOPOLOGY: linear (xi) SEQUENCE DESCRIPTION: SEQ ID NO:34:

```
Met Glu Ser Lys Ala Leu Leu Ala Val Ala Leu Trp Phe Cys Val Glu
1               5                   10                  15

Thr Arg Ala Ala Ser Val Gly Leu Pro Gly Asp Phe Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
            100                 105                 110

Ala Ser Thr Val Tyr Val Tyr Val Arg Asp Tyr Arg Ser Pro Phe Ile
        115                 120                 125

Ala Ser Val Ser Asp Gln His Gly Ile Val Tyr Ile Thr Glu Asn Lys
130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
            180                 185                 190

Met Ile Ser Tyr Ala Gly Met Val Phe Cys Glu Ala Lys Ile Asn Asp
        195                 200                 205

Glu Thr Tyr Gln Ser Ile Met Tyr Ile Val Val Val Gly Tyr Arg
210                 215                 220

Ile Tyr Asp Val Ile Leu Ser Pro Pro His Glu Ile Glu Leu Ser Ala
225                 230                 235                 240

Gly Glu Lys Leu Val Leu Asn Cys Thr Ala Arg Thr Glu Leu Asn Val
                245                 250                 255

Gly Leu Asp Phe Thr Trp His Ser Pro Pro Ser Lys Ser His His Lys
            260                 265                 270

Lys Ile Val Asn Arg Asp Val Lys Pro Phe Pro Gly Thr Val Ala Lys
        275                 280                 285

Met Phe Lys Ser Thr Leu Thr Ile Glu Ser Val Thr Lys Ser Asp Gln
290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                325                 330                 335

Gly Met Lys Ser Leu Val Glu Ala Thr Val Gly Ser Gln Val Arg Ile
            340                 345                 350

Pro Val Lys Tyr Leu Ser Tyr Pro Ala Pro Asp Ile Lys Trp Tyr Arg
        355                 360                 365

Asn Gly Arg Pro Ile Glu Ser Asn Tyr Thr Met Ile Val Gly Asp Glu
```

-continued

```
            370                 375                 380
Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
                405                 410                 415

Leu Val Val Asn Val Pro Pro Gln Ile Gly Glu Lys Ala Leu Ile Ser
                420                 425                 430

Pro Met Asp Ser Tyr Gly Tyr Gly Thr Met Gln Thr Leu Thr Cys Thr
                435                 440                 445

Val Tyr Ala Asn Pro Pro Leu His His Ile Gln Trp Tyr Trp Gln Leu
        450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Gly Asn Lys Ile Glu
                485                 490                 495

Val Thr Lys Asn Gln Tyr Ala Leu Ile Glu Gly Lys Asn Lys Thr Val
                500                 505                 510

Ser Thr Leu Val Ile Gln Ala Ala Asn Val Ser Ala Leu Tyr Lys Cys
        515                 520                 525 lu Ala Ile Asn Lys Ala Gly Arg Gly Glu Arg Val Ile Ser Phe His
        530                 535                 540

Val Ile Arg Gly Pro Glu Ile Thr Val Gln Pro Ala Ala Gln Pro Thr
545                 550                 555                 560

Glu Gln Glu Ser Val Ser Leu Leu Cys Thr Ala Asp Arg Asn Thr Phe
                565                 570                 575

Glu Asn Leu Thr Trp Tyr Lys Leu Gly Ser Gln Ala Thr Ser Val His
                580                 585                 590

Met Gly Glu Ser Leu Thr Pro Val Cys Lys Asn Leu Asp Ala Leu Trp
        595                 600                 605

Lys Leu Asn Gly Thr Met Phe Ser Asn Ser Thr Asn Asp Ile Leu Ile
        610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
                645                 650                 655

Leu Ile Ile Leu Glu Arg Met Ala Pro Met Ile Thr Gly Asn Leu Glu
                660                 665                 670

Asn Gln Thr Thr Thr Ile Gly Glu Thr Ile Glu Val Thr Cys Pro Ala
        675                 680                 685

Ser Gly Asn Pro Thr Pro His Ile Thr Trp Phe Lys Asp Asn Glu Thr
        690                 695                 700

Leu Val Glu Asp Ser Gly Ile Val Leu Arg Asp Gly Asn Arg Asn Leu
705                 710                 715                 720

Thr Ile Arg Arg Val Arg Lys Glu Asp Gly Gly Leu Tyr Thr Cys Gln
                725                 730                 735

Ala Cys Asn Val Leu Gly Cys Ala Arg Ala Glu Thr Leu Phe Ile Ile
                740                 745                 750

Glu Gly Ala Gln Glu Lys Thr Asn Leu Glu Val Ile Ile Leu Val Gly
        755                 760                 765

Thr Ala Val Ile Ala Met Phe Phe Trp Leu Leu Leu Val Ile Leu Val
        770                 775                 780

Arg Thr Val Lys Arg Ala Asn Glu Gly Glu Leu Lys Thr Gly Tyr Leu
785                 790                 795                 800
```

Ser Ile Val Met Asp
            805

(2) INFORMATION FOR SEQ ID NO:35:

(i) SEQUENCE CHARACTERISTICS:
        (A) LENGTH: 2431 base pairs
        (B) TYPE: nucleic acid
        (C) STRANDEDNESS: single
        (D) TOPOLOGY: linear (xi) SEQUENCE DESCRIPTION: SEQ ID NO:35:

```
AGACGTCATG GAGAGCAAGG CGCTGCTAGC TGTCGCTCTG TGGTTCTGCG TGGAGACCCG      60

AGCCGCCTCT GTGGGTTTGC CTGGCGATTT TCTCCATCCC CCCAAGCTCA GCACACAGAA     120

AGACATACTG ACAATTTTGG CAAATACAAC CCTTCAGATT ACTTGCAGGG ACAGCGGGA     180

CCTGGACTGG CTTTGGCCCA ATGCTCAGCG TGATTCTGAG GAAAGGGTAT TGGTGACTGA     240

ATGCGGCGGT GGTGACAGTA TCTTCTGCAA AACACTCACC ATTCCCAGGG TGGTTGGAAA     300

TGATACTGGA GCCTACAAGT GCTCGTACCG GGACGTCGAC ATAGCCTCCA CTGTTTATGT     360

CTATGTTCGA GATTACAGAT CACCATTCAT CGCCTCTGTC AGTGACCAGC ATGGCATCGT     420

GTACATCACC GAGAACAAGA ACAAAACTGT GGTGATCCCC TGCCGAGGGT CGATTTCAAA     480

CCTCAATGTG TCTCTTTGCG CTAGGTATCC AGAAAAGAGA TTTGTTCCGG ATGGAAACAG     540

AATTTCCTGG GACAGCGAGA TAGGCTTTAC TCTCCCCAGT TACATGATCA GCTATGCCGG     600

CATGGTCTTC TGTGAGGCAA AGATCAATGA TGAAACCTAT CAGTCTATCA TGTACATAGT     660

TGTGGTTGTA GGATATAGGA TTTATGATGT GATTCTGAGC CCCCCGCATG AAATTGAGCT     720

ATCTGCCGGA GAAAAACTTG TCTTAAATTG TACAGCGAGA ACAGAGCTCA ATGTGGGGCT     780

TGATTTCACC TGGCACTCTC CACCTTCAAA GTCTCATCAT AAGAAGATTG TAAACCGGGA     840

TGTGAAACCC TTTCCTGGGA CTGTGGCGAA GATGTTTTTG AGCACCTTGA CAATAGAAAG     900

TGTGACCAAG AGTGACCAAG GGAATACAC CTGTGTAGCG TCCAGTGGAC GGATGATCAA      960

GAGAAATAGA ACATTTGTCC GAGTTCACAC AAAGCCTTTT ATTGCTTTCG GTAGTGGGAT    1020

GAAATCTTTG GTGGAAGCCA CAGTGGGCAG TCAAGTCCGA ATCCCTGTGA AGTATCTCAG    1080

TTACCCAGCT CCTGATATCA AATGGTACAG AAATGGAAGG CCCATTGAGT CCAACTACAC    1140

AATGATTGTT GGCGATGAAC TCACCATCAT GGAAGTGACT GAAAGAGATG CAGGAAACTA    1200

CACGGTCATC CTCACCAACC CCATTTCAAT GGAGAAACAG AGCCACATGG TCTCTCTGGT    1260

TGTGAATGTC CCACCCCAGA TCGGTGAGAA AGCCTTGATC TCGCCTATGG ATTCCTACCA    1320

GTATGGGACC ATGCAGACAT TGACATGCAC AGTCTACGCC AACCCTCCCC TGCACCACAT    1380

CCAGTGGTAC TGGCAGCTAG AAGAAGCCTG CTCCTACAGA CCCGGCCAAA CAAGCCCGTA    1440

TGCTTGTAAA GAATGGAGAC ACGTGGAGGA TTTCCAGGGG GGAAACAAGA TCGAAGTCAC    1500

CAAAAACCAA TATGCCCTGA TTGAAGGAAA AAACAAAACT GTAAGTACGC TGGTCATCCA    1560

AGCTGCCAAC GTGTCAGCGT TGTACAAATG TGAAGCCATC AACAAAGCGG GACGAGGAGA    1620

GAGGGTCATC TCCTTCCATG TGATCAGGGG TCCTGAAATT ACTGTGCAAC CTGCTGCCCA    1680

GCCAACTGAG CAGGAGAGTG TGTCCCTGTT GTGCACTGCA GACAGAAATA CGTTTGAGAA    1740

CCTCACGTGG TACAAGCTTG GCTCACAGGC AACATCGGTC CACATGGGCG AATCACTCAC    1800

ACCAGTTTGC AAGAACTTGG ATGCTCTTTG GAAACTGAAT GCCACCATGT TTTCTAACAG    1860

CACAAATGAC ATCTTGATTG TGGCATTTCA GAATGCCTCT CTGCAGGACC AAGGCGACTA    1920
```

```
TGTTTGCTCT GCTCAAGATA AGAAGACCAA GAAAAGACAT TGCCTGGTCA AACAGCTCAT    1980

CATCCTAGAG CGCATGGCAC CCATGATCAC CGGAAATCTG GAGAATCAGA CAACAACCAT    2040

TGGCGAGACC ATTGAAGTGA CTTGCCCAGC ATCTGGAAAT CCTACCCCAC ACATTACATG    2100

GTTCAAAGAC AACGAGACCC TGGTAGAAGA TTCAGGCATT GTACTGAGAG ATGGGAACCG    2160

GAACCTGACT ATCCGCAGGG TGAGGAAGGA GGATGGAGGC CTCTACACCT GCCAGGCCTG    2220

CAATGTCCTT GGCTGTGCAA GAGCGGAGAC GCTCTTCATA ATAGAAGGTG CCCAGGAAAA    2280

GACCAACTTG GAAGTCATTA TCCTCGTCGG CACTGCAGTG ATTGCCATGT TCTTCTGGCT    2340

CCTTCTTGTC ATTCTCGTAC GGACCGTTAA GCGGGCCAAT GAAGGGGAAC TGAAGACAGG    2400

CTACTTGTCT ATTGTCATGG ATTAAGACGT C                                  2431

(2) INFORMATION FOR SEQ ID NO:36:

(i) SEQUENCE CHARACTERISTICS:
         (A) LENGTH: 185 amino acids
         (B) TYPE: amino acid
         (D) TOPOLOGY: linear (xi) SEQUENCE DESCRIPTION: SEQ ID NO:36:

Met His Thr His Gln Asp Phe Gln Pro Val Leu His Leu Val Ala Leu
1               5                   10                  15

Asn Thr Pro Leu Ser Gly Gly Met Arg Gly Ile Arg Gly Ala Asp Phe
            20                  25                  30

Gln Cys Phe Asn Asn Ala Arg Val Gly Leu Ser Gly Thr Phe Arg Ala
        35                  40                  45

Phe Leu Ser Ser Arg Leu Gln Asp Leu Tyr Ser Ile Val Arg Arg Ala
50                  55                  60

Asp Arg Gly Ser Val Pro Ile Val Gln Asn Leu Arg Asp Glu Val Leu
65                  70                  75                  80

Ser Pro Ser Trp Asp Ser Leu Phe Ser Gly Ser Gln Gly Gln Leu Gln
                85                  90                  95

Pro Gly Ala Arg Ile Phe Ser Phe Asp Gly Arg Asp Val Leu Arg His
            100                 105                 110

Pro Ala Trp Pro Gln Arg Ser Val Trp His Gly Ser Asp Pro Ser Gly
        115                 120                 125

Arg Arg Leu Met Glu Ser Tyr Cys Glu Thr Trp Arg Thr Glu Thr Thr
130                 135                 140

Gly Ala Thr Gly Gln Ala Ser Ser Leu Leu Ser Gly Arg Leu Leu Glu
145                 150                 155                 160

Gln Arg Ala Ala Ser Cys His Asp Ser Tyr Ile Val Leu Cys Ile Glu
                165                 170                 175

Asn Ser Phe Met Thr Ser Phe Ser Arg
            180                 185

(2) INFORMATION FOR SEQ ID NO:37:

(i) SEQUENCE CHARACTERISTICS:
         (A) LENGTH: 565 base pairs
         (B) TYPE: nucleic acid
         (C) STRANDEDNESS: single
         (D) TOPOLOGY: linear (xi) SEQUENCE DESCRIPTION: SEQ ID NO:37:

AGACGTCATG CATACTCATC AGGACTTTCA GCCAGTGCTC CACCTGGTGG CACTGAACAC      60

CCCCCTGTCT GGAGGCATGC GTGGTATCCG TGGAGCAGAT TTCCAGTGCT TCCAGCAAGC     120
```

```
CCGAGCCGTG GGGCTGTCGG GCACCTTCCG GGCTTTCCTG TCCTCTAGGC TGCAGGATCT     180

CTATAGCATC GTGCGCCGTG CTGACCGGGG GTCTGTGCCC ATCGTCAACC TGAAGGACGA     240

GGTGCTATCT CCCAGCTGGG ACTCCCTGTT TTCTGGCTCC CAGGGTCAAC TGCAACCCGG     300

GGCCCGCATC TTTTCTTTTG ACGGCAGAGA TGTCCTGAGA CACCCAGCCT GGCCGCAGAA     360

GAGCGTATGG CACGGCTCGG ACCCCAGTGG GCGGAGGCTG ATGGAGAGTT ACTGTGAGAC     420

ATGGCGAACT GAAACTACTG GGCTACAGG TCAGGCCTCC TCCCTGCTGT CAGGCAGGCT      480

CCTGGAACAG AAAGCTGCGA GCTGCCACAA CAGCTACATC GTCCTGTGCA TTGAGAATAG    540

CTTCATGACC TCTTTCTCCA AATAG                                          565
```

(2) INFORMATION FOR SEQ ID NO:38:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
CTATCGTCGA CATGTATATT GGTTCTCGTT AAGTCGACCT ATC                       43
```

(2) INFORMATION FOR SEQ ID NO:39:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
GATAGGTCGA CTTAACGAGA ACCAATATAC ATGTCGACGA TAG                       43
```

(2) INFORMATION FOR SEQ ID NO:40:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:40:

```
AGTATCTAGA ATGAGTGTAT CTGTCACAAT G                                    31
```

(2) INFORMATION FOR SEQ ID NO:41:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:41:

```
GAATTCTAGA TCACCTATGA GGGGTTTGCT C                                    31
```

(2) INFORMATION FOR SEQ ID NO:42:

(i) SEQUENCE CHARACTERISTICS:
        (A) LENGTH: 93 base pairs
        (B) TYPE: nucleic acid
        (C) STRANDEDNESS: single -continued

```
        (D) TOPOLOGY: linear (xi) SEQUENCE DESCRIPTION: SEQ ID NO:42:

CTATCGTCGA CATGTATATT GGTTCTCGTA AAAGATATAT TGGTTCTCGT GGTAAAAGAG        60

ATGGTTCTCG TGGTAAAAGA TAAGTGACCT ATC                                    93

(2) INFORMATION FOR SEQ ID NO:43:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (xi) SEQUENCE DESCRIPTION: SEQ ID NO:43:

GATAGGTCGA CTTAT                                                         15
```